US011730668B2

(12) United States Patent
Wersland et al.

(10) Patent No.: US 11,730,668 B2
(45) Date of Patent: Aug. 22, 2023

(54) VIBRATING THERAPY SYSTEM AND DEVICE

(71) Applicant: Therabody, Inc., Los Angeles, CA (US)

(72) Inventors: Jason Wersland, Los Angeles, CA (US); Benjamin Nazarian, Los Angeles, CA (US); Jaime Sanchez Solana, Los Angeles, CA (US); Eduardo Merino, Los Angeles, CA (US); Bill Webb, San Francisco, CA (US); Alex Zhu, Xiamen (CN); Richard Tang, Shenzhen (CN)

(73) Assignee: Therabody, Inc., Los Angeles, CA (US)

( * ) Notice: Subject to any disclaimer, the term of this patent is extended or adjusted under 35 U.S.C. 154(b) by 0 days.

(21) Appl. No.: 17/705,300

(22) Filed: Mar. 26, 2022

(65) Prior Publication Data

US 2022/0211575 A1  Jul. 7, 2022

Related U.S. Application Data

(63) Continuation-in-part of application No. 17/361,966, filed on Jun. 29, 2021, now Pat. No. 11,331,244.

(Continued)

(51) Int. Cl.
*A61H 23/00* (2006.01)
*A61H 23/02* (2006.01)
(Continued)

(52) U.S. Cl.
CPC ........ *A61H 23/0254* (2013.01); *A61H 23/006* (2013.01); *A61H 23/0218* (2013.01);
(Continued)

(58) Field of Classification Search
CPC ........ A61H 23/00; A61H 23/006; A61H 7/00; A61H 15/02; A46B 13/02;
(Continued)

(56) References Cited

U.S. PATENT DOCUMENTS 1,955,863 A  4/1934 Schmidt
2,183,726 A  12/1939 Sommer
(Continued)

FOREIGN PATENT DOCUMENTS

KR  20200051098 A  *  5/2020
WO  2019097291  5/2019
(Continued)

OTHER PUBLICATIONS

International Search Report and Written Opinion issued in PCT/US21/39586 dated 2021.

*Primary Examiner* — Justine R Yu
*Assistant Examiner* — Christopher E Miller
(74) *Attorney, Agent, or Firm* — Sterne, Kessler, Goldstein & Fox P.L.L.C.

(57) ABSTRACT

A vibration therapy device that includes a housing that includes a handle portion, a head portion and a module seat defined on the head portion, an electrical source, a motor positioned in the housing, a switch for activating the motor, a push rod assembly operatively connected to the motor and configured to reciprocate in response to activation of the motor, and a therapy module removably secured to the module seat. The distal end of the push rod assembly is configured to removably receive a reciprocating attachment thereon. The therapy module at least partially surrounds the distal end of the push rod assembly.

19 Claims, 21 Drawing Sheets

Related U.S. Application Data

(60) Provisional application No. 63/133,530, filed on Jan. 4, 2021, provisional application No. 63/065,348, filed on Aug. 13, 2020, provisional application No. 63/045,365, filed on Jun. 29, 2020.

(51) Int. Cl.
- *A61N 1/32* (2006.01)
- *A61F 7/00* (2006.01)
- *A61N 5/06* (2006.01)

(52) U.S. Cl.
CPC ....... *A61F 7/007* (2013.01); *A61F 2007/0075* (2013.01); *A61H 2201/0107* (2013.01); *A61H 2201/0153* (2013.01); *A61H 2201/0207* (2013.01); *A61H 2201/0214* (2013.01); *A61H 2201/0285* (2013.01); *A61H 2201/10* (2013.01); *A61H 2201/123* (2013.01); *A61H 2201/1669* (2013.01); *A61H 2201/1685* (2013.01); *A61H 2205/022* (2013.01); *A61N 1/328* (2013.01); *A61N 5/0616* (2013.01); *A61N 2005/0652* (2013.01); *A61N 2005/0659* (2013.01); *A61N 2005/0663* (2013.01)

(58) Field of Classification Search
CPC ........... A46B 2200/102; A61M 35/003; A61N 2005/0644; A61N 5/0616; A61F 2007/0087

See application file for complete search history.

(56) References Cited

U.S. PATENT DOCUMENTS

| | | | |
|---|---|---|---|
| 4,088,128 A * | 5/1978 | Mabuchi | A61H 23/0254 601/108 |
| 4,513,737 A * | 4/1985 | Mabuchi | A61H 23/0254 601/108 |
| 4,858,600 A | 8/1989 | Gross | |
| 5,103,809 A | 4/1992 | DeLuca | |
| 5,471,695 A * | 12/1995 | Aiyar | A46B 13/02 601/72 |
| 6,401,289 B1 * | 6/2002 | Herbert | A61H 7/005 601/114 |
| 6,524,329 B1 | 2/2003 | Benedict | |
| 6,535,761 B2 | 3/2003 | Bernabei | |
| 6,743,215 B2 | 6/2004 | Bernabei | |
| 6,748,266 B2 | 6/2004 | Bernabei | |
| 6,766,199 B2 | 7/2004 | Cook | |
| 6,974,224 B2 | 12/2005 | Thomas-Benedict | |
| 6,980,854 B2 | 12/2005 | Bernabei | |
| 7,010,343 B2 | 3/2006 | Bernabei | |
| 7,014,639 B2 | 3/2006 | Walneck | |
| 7,083,580 B2 | 8/2006 | Bernabei | |
| 7,204,832 B2 | 4/2007 | Altshuler | |
| 7,258,675 B2 | 8/2007 | Nichols | |
| 7,282,036 B2 | 10/2007 | Masuda | |
| 7,305,269 B2 | 12/2007 | Cook | |
| 7,376,460 B2 | 5/2008 | Bernabei | |
| 7,471,979 B2 | 12/2008 | Bernabei | |
| 7,532,926 B2 | 5/2009 | Bernabei | |
| 8,105,322 B2 | 1/2012 | Ely | |
| 8,157,753 B2 | 4/2012 | Nichols | |
| 8,182,473 B2 | 5/2012 | Altshuler | |
| 8,382,690 B2 | 2/2013 | Yoon | |
| 8,506,506 B2 | 8/2013 | Nebrigic | |
| 8,523,791 B2 | 9/2013 | Castel | |
| 8,540,702 B2 | 9/2013 | Ely | |
| D693,932 S | 11/2013 | Nichols | |
| 8,655,448 B2 | 2/2014 | Cook | |
| 8,696,605 B2 | 4/2014 | Nichols | |
| 8,906,009 B2 | 12/2014 | Nebrigic | |
| 8,945,104 B2 | 2/2015 | Boone, III | |
| 9,023,021 B2 | 5/2015 | Behrakis | |
| 9,042,993 B2 | 5/2015 | Cook | |
| 9,084,587 B2 | 7/2015 | Eckhouse | |
| D736,399 S | 8/2015 | Nichols | |
| 9,272,141 B2 | 3/2016 | Nichols | |
| 9,278,045 B2 | 3/2016 | Scerbo | |
| 9,386,837 B2 | 7/2016 | Geva | |
| D764,173 S | 8/2016 | Nichols | |
| D765,982 S | 9/2016 | Nichols | |
| 9,579,250 B2 | 2/2017 | Nichols | |
| 9,585,687 B2 | 3/2017 | Tenenbaum | |
| D803,572 S | 11/2017 | Nichols | |
| 9,808,646 B2 | 11/2017 | Piergallini | |
| 9,872,813 B2 | 1/2018 | Giraud | |
| 9,925,006 B2 | 3/2018 | Behrakis | |
| 10,016,337 B2 | 7/2018 | Roberts | |
| 10,124,165 B2 | 11/2018 | Gimelli | |
| 10,137,054 B2 | 11/2018 | Giraud | |
| 10,252,051 B2 | 4/2019 | Nichols | |
| 10,376,659 B2 | 4/2019 | Nichols | |
| 10,278,888 B2 | 5/2019 | Sabattier | |
| 10,285,722 B2 | 5/2019 | Favie | |
| 10,307,330 B1 | 6/2019 | Sedic | |
| 10,383,486 B2 | 8/2019 | Nichols | |
| 10,511,777 B2 | 12/2019 | Nichols | |
| 10,518,097 B2 | 12/2019 | Grez | |
| 10,625,093 B2 | 4/2020 | Shenfarber | |
| 10,661,072 B2 | 5/2020 | Kern | |
| 10,695,508 B2 | 6/2020 | Lorberbaum | |
| 10,737,107 B2 | 8/2020 | Ledany | |
| 10,758,452 B2 | 9/2020 | Wersland | |
| 10,821,299 B1 | 11/2020 | Shenfarber | |
| 10,857,064 B2 | 12/2020 | Wersland | |
| 10,881,577 B2 | 1/2021 | Hashimoto | |
| 10,945,915 B2 | 3/2021 | Wersland | |
| 2002/0082536 A1 * | 6/2002 | Tucek | A61H 1/008 601/107 |
| 2004/0030325 A1 | 2/2004 | Cahir | |
| 2004/0147984 A1 | 7/2004 | Altshuler | |
| 2004/0260212 A1 * | 12/2004 | Cho | A61N 1/30 601/72 |
| 2005/0043653 A1 | 2/2005 | Trimmer | |
| 2007/0038206 A1 | 2/2007 | Altshuler | |
| 2007/0179573 A1 | 8/2007 | Laurent | |
| 2007/0198004 A1 | 8/2007 | Altshuler | |
| 2007/0213696 A1 | 9/2007 | Altshuler | |
| 2007/0213698 A1 | 9/2007 | Altshuler | |
| 2007/0239142 A1 | 10/2007 | Altshuler | |
| 2007/0239143 A1 | 10/2007 | Altshuler | |
| 2008/0014011 A1 | 1/2008 | Rossen | |
| 2008/0065176 A1 | 3/2008 | Zhang | |
| 2008/0119913 A1 | 3/2008 | Powell | |
| 2008/0103560 A1 | 5/2008 | Powell | |
| 2008/0103563 A1 | 5/2008 | Powell | |
| 2008/0125835 A1 | 5/2008 | Laurent | |
| 2008/0193493 A1 | 5/2008 | Rhoades | |
| 2008/0215123 A1 | 9/2008 | Maricle | |
| 2008/0234611 A1 * | 9/2008 | Sakai | B01F 23/2351 601/95 |
| 2008/0275532 A1 | 11/2008 | Yamazaki | |
| 2009/0043293 A1 | 2/2009 | Pankratov | |
| 2009/0182249 A1 * | 7/2009 | Sakai | A61H 7/005 601/134 |
| 2009/0234338 A1 | 9/2009 | Roth | |
| 2009/0287195 A1 | 11/2009 | Altshuler | |
| 2010/0121419 A1 | 3/2010 | Douglas | |
| 2010/0137752 A1 | 6/2010 | Heine | |
| 2010/0274162 A1 | 10/2010 | Evans | |
| 2010/0274329 A1 | 10/2010 | Bradley | |
| 2010/0312157 A1 | 12/2010 | Yan | |
| 2011/0040235 A1 | 2/2011 | Castel | |
| 2011/0106067 A1 | 5/2011 | Geva | |
| 2011/0184499 A1 | 7/2011 | Radi | |
| 2012/0065555 A1 | 3/2012 | Chae | |
| 2012/0109041 A1 | 5/2012 | Munz | |
| 2012/0253246 A1 * | 10/2012 | Yamazaki | A61H 39/04 601/101 |
| 2012/0310124 A1 | 12/2012 | Zhang | |
| 2013/0012851 A1 | 1/2013 | Fahmie | |
| 2013/0046212 A1 | 2/2013 | Nichols | |

(56) References Cited

U.S. PATENT DOCUMENTS

| | | | |
|---|---|---|---|
| 2013/0060176 A1 | 3/2013 | Nichols | |
| 2013/0213431 A1* | 8/2013 | Geva | A45D 33/00 132/320 |
| 2014/0031866 A1* | 1/2014 | Fuhr | A61H 1/008 606/239 |
| 2014/0096786 A1* | 4/2014 | Nuzzo | A61H 7/005 132/202 |
| 2014/0128780 A1 | 5/2014 | Kennedy | |
| 2014/0135798 A1 | 5/2014 | David | |
| 2014/0219701 A1 | 8/2014 | Eberlein | |
| 2014/0276255 A1 | 9/2014 | McGushion | |
| 2014/0288364 A1 | 9/2014 | St. Bernard | |
| 2014/0323927 A1 | 10/2014 | Kim | |
| 2014/0336540 A1 | 11/2014 | Chen | |
| 2014/0371637 A1* | 12/2014 | Lee | A61H 23/0245 601/2 |
| 2014/0378555 A1 | 12/2014 | Hung | |
| 2015/0005682 A1* | 1/2015 | Danby | A61H 23/0254 601/101 |
| 2015/0045702 A1 | 2/2015 | Lin | |
| 2015/0100002 A1 | 4/2015 | Choi | |
| 2015/0119771 A1 | 4/2015 | Roberts | |
| 2015/0202114 A1* | 7/2015 | Pardoel | A61H 23/0218 601/112 |
| 2015/0224020 A1 | 8/2015 | Flyash | |
| 2015/0265825 A1 | 9/2015 | Miller | |
| 2015/0283025 A1 | 10/2015 | Ledany | |
| 2015/0297393 A1 | 10/2015 | McGushion | |
| 2015/0305969 A1 | 10/2015 | Giraud | |
| 2016/0184162 A1 | 6/2016 | Grez | |
| 2016/0192814 A1* | 7/2016 | Kang | A47K 7/04 15/21.1 |
| 2016/0287034 A1* | 10/2016 | Woodard | A46B 11/063 |
| 2016/0324719 A1 | 11/2016 | Badmus | |
| 2017/0049278 A1 | 2/2017 | Thomassen | |
| 2017/0056685 A1 | 3/2017 | Harvey | |
| 2017/0072175 A1 | 3/2017 | Batiste | |
| 2017/0128130 A1 | 5/2017 | Giraud | |
| 2017/0189670 A1 | 7/2017 | Brunson | |
| 2017/0202732 A1 | 7/2017 | Nichols | |
| 2017/0238686 A1 | 8/2017 | Sanchez Martinez | |
| 2018/0015299 A1 | 1/2018 | Kawa | |
| 2018/0031089 A1 | 2/2018 | Wong | |
| 2018/0031090 A1 | 2/2018 | Wong | |
| 2018/0050440 A1* | 2/2018 | Chen | B25B 23/0035 |
| 2018/0133470 A1 | 5/2018 | Park | |
| 2018/0168318 A1 | 6/2018 | Streeter | |
| 2018/0185236 A1 | 7/2018 | Levi | |
| 2018/0295980 A1* | 10/2018 | Boersma | A46B 13/008 |
| 2019/0015294 A1* | 1/2019 | Nazarian | A61H 15/00 |
| 2019/0240110 A1 | 8/2019 | Sedic | |
| 2019/0254922 A1 | 8/2019 | Marton | |
| 2019/0262607 A1 | 8/2019 | Nichols | |
| 2019/0290531 A1* | 9/2019 | Bosma | A61F 7/007 |
| 2019/0343712 A1 | 11/2019 | Cheng | |
| 2019/0388707 A1 | 12/2019 | Shenfarber | |
| 2020/0038673 A1 | 2/2020 | Yildirim | |
| 2020/0086137 A1 | 3/2020 | Yoo | |
| 2020/0093945 A1 | 3/2020 | Jeong | |
| 2020/0113322 A1 | 4/2020 | Balestrini | |
| 2020/0129372 A1 | 4/2020 | Tseng | |
| 2020/0154874 A1* | 5/2020 | Tammabattula | A46B 13/023 |
| 2020/0179220 A1 | 6/2020 | Jablow | |
| 2020/0187635 A1* | 6/2020 | Akridge | A46B 13/023 |
| 2020/0215351 A1 | 7/2020 | Shenfarber | |
| 2020/0237085 A1 | 7/2020 | Miller | |
| 2020/0237604 A1 | 7/2020 | Truong | |
| 2020/0253811 A1 | 8/2020 | Alexander | |
| 2020/0268594 A1 | 8/2020 | Pepe | |
| 2020/0280680 A1 | 9/2020 | Nichols | |
| 2020/0288843 A1 | 9/2020 | Verheem | |
| 2020/0352306 A1 | 11/2020 | Um | |
| 2020/0352317 A1 | 11/2020 | Yeates | |
| 2020/0390468 A1 | 12/2020 | Alexander | |
| 2020/0390644 A1* | 12/2020 | Yang | A61H 23/02 |
| 2021/0001148 A1 | 1/2021 | Verheem | |
| 2021/0128402 A1 | 5/2021 | Dai | |

FOREIGN PATENT DOCUMENTS

| | | |
|---|---|---|
| WO | 2019150887 | 8/2019 |
| WO | 2019155210 A2 | 8/2019 |
| WO | 2020028329 | 2/2020 |
| WO | 2020154177 | 7/2020 |
| WO | 2020159727 | 8/2020 |
| WO | 2020163738 | 8/2020 |
| WO | 2020252440 | 12/2020 |

* cited by examiner

VIBRATING THERAPY SYSTEM AND DEVICE

CROSS REFERENCE TO RELATED APPLICATIONS

This application is a continuation-in-part of U.S. patent application Ser. No. 17/361,966, filed Jun. 29, 2021, which claims the benefit of U.S. Provisional Application No. 63/133,530, filed Jan. 4, 2021, U.S. Provisional Application No. 63/065,348, filed Aug. 13, 2020, and U.S. Provisional Patent Application No. 63/045,365, filed Jun. 29, 2020, the entireties of which are incorporated by reference herein.

FIELD OF THE INVENTION

The present invention relates generally to a vibration therapy system and device, and more particularly to a vibration therapy device with interchangeable attachments.

BACKGROUND OF THE INVENTION

As people age, devices for skin and facial care are needed. Percussive massage devices that provide reciprocating motion and provide relief to sore muscles and other parts of the body are known. For example, see U.S. Pat. Nos. 10,857,064 and 10,945,915, the entireties of which are incorporated by reference herein. However, many percussive massage devices may be uncomfortable if used on the face and principally target the underlying muscles. The present invention addresses the needs discussed herein.

The background description disclosed anywhere in this patent application includes information that may be useful in understanding the present invention. It is not an admission that any of the information provided herein is prior art or relevant to the presently claimed invention, or that any publication specifically or implicitly referenced is prior art.

SUMMARY OF THE PREFERRED EMBODIMENTS

In accordance with a first aspect of the present invention there is provided a vibration therapy device that includes a housing with a handle portion and a head portion, an electrical source, a motor positioned in the housing, a switch for activating the motor, a push rod assembly operatively connected to the motor, and a reciprocating attachment. The push rod assembly includes an attachment member that defines the distal end of the push rod assembly. The attachment member (or the reciprocating attachment secured to the attachment member) is configured to reciprocate in response to activation of the motor at a linear velocity between 0.06 m/s and 0.5 m/s. The attachment member includes a first magnet. The reciprocating attachment is removably received on the attachment member. The reciprocating attachment includes a second magnet that is magnetically attracted to the first magnet to secure the reciprocating attachment on the attachment member.

In a preferred embodiment, the reciprocating attachment includes an attachment member recess defined therein. The attachment member is received in the attachment member recess. The attachment member defines an attachment member diameter and the attachment member recess defines an attachment member recess diameter. The attachment member diameter is smaller than the attachment member recess diameter. The first and second magnets secure the reciprocating attachment on the attachment member during reciprocation. Preferably, a module seat is defined on the head portion and a ring module is removably secured to the module seat. The ring module includes a central opening that defines a central opening diameter. The attachment member defines an attachment member diameter. The central opening diameter is larger than the attachment member diameter, such that the reciprocating attachment is configured to reciprocate within and relative to the ring module.

In accordance with another aspect of the present invention there is provided a therapy device that includes a housing that includes a handle portion, a head portion and a module seat defined on the head portion. The module seat includes a first set of magnets associated therewith (on, in or adjacent to the module seat). The module seat includes a first securement protrusion extending therefrom and includes a first securement recess defined therein. The therapy device also includes an electrical source, and a therapy module removably secured to the module seat. The therapy module includes a second set of magnets that are magnetically attracted to the first set of magnets. The therapy module includes a second securement protrusion extending therefrom and includes a second securement recess defined therein. The first securement protrusion is received in the second securement recess. The second securement protrusion is received in the first securement recess. This type of therapy device may not include the reciprocating, vibration or percussive feature.

In a preferred embodiment, one of the first securement protrusion and the second securement recess includes female electrical contacts and the other of the first securement protrusion and second securement recess includes male electrical contacts. Connection of the male electrical contacts and female electrical contacts provides electrical communication between the electrical source and the therapy module. The therapy module may provide at least one of cold therapy, heat therapy, LED light therapy, microcurrent therapy, photobiomodulation therapy, radio frequency therapy, cleansing therapy or ultrasound therapy.

The therapy device may include a motor positioned in the housing, a switch for activating the motor, and a push rod assembly operatively connected to the motor. The push rod assembly includes an attachment member that defines the distal end of the push rod assembly. The therapy module includes a central opening defined therein, and the attachment member extends into the central opening. In a preferred embodiment, the male electrical contacts include four prongs. Two of the prongs provide electrical communication and two of the prongs provide data communication.

In accordance with another aspect of the present invention there is provided a vibration therapy device that includes a housing that includes a handle portion and a head portion, an electrical source, a motor positioned in the housing, a switch for activating the motor, a push rod assembly operatively connected to the motor and that includes a reciprocating shaft with an attachment member secured to its distal end, and a flexible sleeve that includes a proximal end and a distal end. The flexible sleeve at least partially surrounds the reciprocating shaft. The distal end of the flexible sleeve is secured to the attachment member and the proximal end of the flexible sleeve is secured to the housing.

The reciprocating shaft may include an opening in a distal end thereof. The attachment member may include a shaft that is received in the opening in the reciprocating shaft. The distal end of the flexible sleeve may be secured between the distal end of the reciprocating shaft and the attachment member. The housing preferably includes a protrusive portion. The proximal end of the flexible sleeve is secured by the protrusive portion. The sleeve may include an annular ridge extending therefrom that is received in a groove in the housing.

In accordance with another aspect of the present invention there is provided a vibration therapy device that includes a housing that includes a handle portion, a head portion and a module seat defined on the head portion, an electrical source, a motor positioned in the housing, a switch for activating the motor, and a push rod assembly operatively connected to the motor. The module seat includes a first set of magnets. The push rod assembly includes an attachment member at a distal end thereof that is configured to reciprocate in response to activation of the motor. The attachment member includes a first magnet. The vibration therapy device also includes a cleansing attachment removably received on the attachment member. The cleansing attachment includes a second magnet that is magnetically attracted to the first magnet to secure the reciprocating attachment on the attachment member. The cleansing attachment includes a second set of magnets that are magnetically attracted to the first set of magnets to removably secure the cleansing attachment to the module seat. The cleansing attachment includes a central section, such that when the attachment member reciprocates, the central section flexes. Preferably, the module seat includes a first securement protrusion extending therefrom and includes a first securement recess defined therein, the cleansing attachment includes a second securement protrusion extending therefrom and includes a second securement recess defined therein and the first securement protrusion is received in the second securement recess, and wherein the second securement protrusion is received in the first securement recess.

In accordance with another aspect of the present invention there is provided a vibration therapy device that includes a housing that includes a handle portion, a head portion and a module seat defined on the head portion, an electrical source, a motor positioned in the housing, a switch for activating the motor, a push rod assembly operatively connected to the motor and configured to reciprocate in response to activation of the motor, and a therapy module removably secured to the module seat. The distal end of the push rod assembly is configured to removably receive a reciprocating attachment thereon. The therapy module at least partially surrounds the distal end of the push rod assembly. In a preferred embodiment, the push rod assembly includes an attachment member that defines the distal end of the push rod assembly. The therapy module is coaxial with the distal end of the push rod assembly (e.g., the attachment member and/or the magnet seat), and at least a portion of the attachment member (e.g., the magnet member) extends into the therapy module.

In a preferred embodiment, the therapy module is in electrical communication with the electrical source (so that it can be powered) and/or is in data communication with the controller/processor of the device (so that it can be operated as desired). For electrical connection, the module seat preferably includes a first electrical connector (male or female), and wherein the therapy module includes a second electrical connector (female or male) in electrical communication with the first electrical connector. In a preferred embodiment, the male electrical connector includes a plurality of prongs, two of which are used for the electrical connection or communication (positive voltage and negative voltage) and two of which are used for data or information connection or communication (control signal). The prongs are inserted into the female electrical connector, which includes four openings for receiving the four prongs. The therapy module may comprise a ring module that includes a central opening and an outer surface. When a reciprocating attachment that includes a contact surface is removably received on the distal end of the push rod assembly, the contact surface of the reciprocating attachment extends further from the module seat than the outer surface of the ring module.

The therapy module may be a ring module that includes a plurality of LED's therein or thereon. The LEDs are configured to operate at a treatment level only when the outer surface is less than a predetermined distance from an operating surface. In a preferred embodiment, the ring module further includes at least first and second proximity sensors that are positioned approximately 180° from one another within the ring module (e.g., on the PCB). The first and second proximity sensors are each configured to activate the LEDs at the treatment level when the outer surface of the ring module is less than the predetermined distance from the operating surface.

The therapy module may comprise a cap module that includes a main body portion and a rear recess and where at least a portion of the attachment member extends into the rear recess. The cap module may include an anode and a cathode and may be configured to provide micro-current therapy. The cap module may also be configured to be removably secured to the module seat and the attachment member. In this embodiment, the cap module may be removably secured to the module seat via magnets and/or one or more securement protrusions and recesses (that also help properly align the cap module).

In accordance with another aspect of the invention there is provided a vibration therapy system that includes a vibration therapy device, a ring module that includes a central opening and that is configured to be removably secured to the module seat, a cap module that includes a main body portion and a rear recess and that is configured to be removably secured to the module seat, and a reciprocating attachment that is configured to be removably received on the attachment member. When the ring module is removably secured to the module seat, the distal end of the push rod assembly extends into the central opening. When the cap module is removably secured to the module seat, the distal end of the push rod assembly extends into the rear recess. When the ring module is received on the module seat, the reciprocating attachment extends through the central opening. When the ring module is received on the module seat the attachment member can be reciprocated, and when the cap module is received on the module seat the attachment member cannot be reciprocated.

In accordance with another aspect of the invention there is provided a vibration therapy device that includes a housing that includes a handle portion and a head portion an electrical source, a motor positioned in the housing, a switch for activating the motor, a push rod assembly operatively connected to the motor and configured to reciprocate in response to activation of the motor, and a reciprocating attachment removably secured to a distal end of the push rod assembly. The reciprocating attachment includes a contact surface, and a skin treatment member is removably secured to the reciprocating attachment such that a delivery portion at least partially covers the contact surface. In a preferred embodiment, the reciprocating attachment includes a groove defined therein and at least a portion of the skin treatment member is received in the groove. Preferably, the skin treatment member includes a main body portion that, together with the delivery portion, defines an attachment recess. At least one ridge member extends inwardly from the main body portion into the attachment recess and is received in the groove on the reciprocating attachment. In a preferred embodiment, the delivery portion includes a lotion or other formulation thereon.

Described herein is a vibration therapy device that includes interchangeable attachments that provide therapy to a user. The interchangeable attachments can include, for example, LED light therapy, micro-current, etc. Generally, the present invention is a vibration therapy device that includes LED lights thereon that can be used for skin therapy. LED skin therapy is known. For example, see U.S. Pat. Nos. 6,524,329 and 6,974,224, the entireties of which are incorporated by reference herein.

The present invention is a hand-held vibration facial massager or vibration therapy device that includes different therapy attachments compatible therewith. The hand-held device, which is intended to be used on the face, but can also be used anywhere else on the body, combines vibration therapy with other facial treatment technologies, including, but not limited to, LED light therapy, micro-current treatments and radio frequency skin technology.

As discussed below, the vibration therapy treatment can be delivered by a brushless motor-drive train system with the distal end of the reciprocating output shaft including an amplitude of preferably between 2.0 mm and 8.0 mm. It will be appreciated that this small amplitude of reciprocation is referred to herein as a vibrating movement or vibration, hence the phrase "vibration therapy device." However, the amplitude can be anywhere between 1.0 mm and 25 mm. In a preferred embodiment, the amplitude is about 3.0 mm and the device provides the ability to operate at at least three different frequencies, e.g., 1750 (percussions per minute) ppm or 29 Hz, 2100 ppm or 35 Hz and 2400 ppm or 40 Hz. However, the frequency can be anywhere between about 900 ppm or 15 Hz and about 6000 ppm or 100 Hz. The combination of the about 3.0 amplitude and the frequencies between 1750 ppm and 2400 ppm is optimized for the face. The percussive therapy provided with these specifications helps reduce minor facial muscle pain and tension, helps reduce muscle tension often associated with headaches (this includes muscles of face, neck, and head) and provides a facial massage to reduce tension and relax facial muscles.

The removable or interchangeable vibration therapy attachment on the end of the output shaft can be any type of attachment (see, e.g., the patents discussed above). In a preferred embodiment, the attachment is a foam/rubber attachment that is connected to the end of the shaft to deliver the vibration to the user's face. See, e.g., U.S. Pat. No. 10,758,452, the entirety of which is incorporated by reference herein.

The present invention includes an attachment system to accommodate swappable or interchangeable rings or modules with different facial treatment technologies. For example, the module can be a blue, red, amber and/or infrared LED light therapy light ring module or can be a module that includes micro-current therapy, RF (radio frequency) therapy, heat, cold, electric stimulation and/or vibration (e.g., the therapy module can include one or more motors or the like that provide vibration, separate from the reciprocation of the reciprocating attachment). As discussed below, in a preferred embodiment, the device includes an electrical connection system to deliver electric power to the ring or module and a magnet-based system to secure the ring or module in place.

In one preferred embodiment, the magnets are programmed or polymagnets. Polymagnets are magnetic structures that incorporate correlated patterns of magnets with alternating polarity, designed to achieve a desired behavior and deliver stronger local force. By varying the magnetic fields and strengths, different mechanical behaviors can be controlled. Correlated magnet pairs can be programmed to attract or repel with a prescribed force and engagement distance, or, to attract or repel at a certain spatial orientation. Correlated magnets can be programmed to interact only with other magnetic structures that have been coded to respond. As a result, a strong force can be used to hold the module on the device, but a fairly weak force can be used for removing the module. For example, the user can rotate the module about the module's central axis to a predetermined point where the module can be easily removed. The polymagnets in the device can even repel the polymagnets in the module at a certain rotation point, thus making removal of the module very easy. The polymagnets change properties based on the distance and position of the magnets in the ring module and the device with respect to one another. This allows the locking and unlocking forces that the user needs to apply to connect and disconnect the module from the device to be reduced compared to the use of regular magnets. For example: the magnets can repel each other when the distance between them is more than one inch but if they are brought closer than one inch they attract each other. Therefore, for example, at a first distance and a first degree of rotation, the force required to secure the module or push the module into place on the module seat (referred to herein as "attach the module") is X and at the first distance and a second degree of rotation, the force required to attach the module is Y, where Y is less than X. To detach the module or pull it off the device, the force required may be A at a first set of degrees of rotation and B at a second set of degrees of rotation, where A is less than B. For example, the first set of degrees of rotation may be 0° to 15° and the second set of degrees of rotation may be 16° to 360°. Therefore, when the module or attachment is rotated to an angle between 0° to 15° it is easy to remove. At any other angle it is difficult for the user to remove.

In a preferred embodiment, the device and/or system also includes a software application downloadable to a portable electronic device that includes the ability to control the treatment and build different protocols via Bluetooth and the like.

In a preferred embodiment, the device and/or the therapy module includes a proximity sensor that detects the distance between the device and the user's face so that the therapy or treatment can be modified accordingly. For example, the light ring module can include one or more proximity sensors so that the LED lights can be dimmed and/or turned off when the device is pulled away from the user's skin and is not within a predetermined distance (i.e., when the ring is far enough from the user's face that no treatment is being provided). This may be done to save battery, for eye safety purposes or for other skin safety issues or concerns.

In a preferred embodiment, the handle forms an angle of about 120 degrees with the attachment arm or output shaft to avoid blocking the user's view during treatment. In a preferred embodiment, the housing includes a female charging jack for receiving a male connector and charging the battery. The device also includes one or more buttons or switches for controlling the device (e.g., on/off, speed control, change color of LEDs, etc.) and LEDs that provide indication of different functions, such as battery power or speed setting, etc.

In a preferred embodiment, the vibration therapy device includes a motor, battery, housing, and push rod assembly with a reciprocating shaft. The reciprocating shaft includes a male or female attachment member on the end thereof to which a massage or vibration attachment (that includes a corresponding female or male attachment member thereon) can be attached. In a preferred embodiment, the massage attachment is secured to the vibration therapy device using magnets. When the device is used with a ring module or attachment vibration attachment extends through the center of the ring. Any type of attaching or securing arrangement between the massage attachment and the vibration therapy device is within the scope of the invention. In a preferred embodiment, the amplitude is between about 2 mm and about 8 mm, which is smaller than many percussive massage devices. However, in another embodiment, the amplitude can be greater and between 1 mm and 26 mm or more.

In a preferred embodiment, the motor converts power from the power source into motion. In some embodiments, the motor is an electric motor. The electric motor may be any type of electric motor known in the art, including, but not limited to, a brushed motor, a brushless motor, a direct current (DC) motor, an alternating current (AC) motor, a mechanical-commutator motor, an electronic commutator motor, or an externally commutated motor. In a preferred embodiment, the motor is a brushless direct-current (BLDC) motor. Preferably, the percussive massage device includes a voltage-sensing resistor electrically coupled to the BLDC motor and a controller.

In a preferred embodiment, the vibration therapy device includes a removable light ring therapy module that surrounds the massage or reciprocating attachment. In a preferred embodiment, the light ring module includes a plurality of lights (e.g., LED's). Preferably, the light ring module is electrically connected to the vibration therapy device when it is attached thereto so that the battery powers the lights. The light ring module includes a central opening that at least partially surrounds the reciprocating attachment.

In a preferred embodiment, a plurality of different ring modules are included either separately or sold as a kit with the vibration therapy device. For example, separate ring modules can include lights with different wavelengths (e.g., red LEDs on one ring and blue LEDs on another). In another embodiment, lights with different wavelengths can be included on the same ring (e.g., blue and red LEDs on the same ring). The rings are interchangeable. The rings can be different sizes. Each of the ring modules can provide different functions or features. Some of the features can be used in conjunction with the vibration therapy massage attachment and others can be used with a massage attachment attached to the device. For example, the ring modules can include (either individually or in combination) heat, vibrations, electrodes for electrolysis and/or emitting electromagnetic pulses. As a result, the main device acts as a power source for powering all of the different ring modules and the therapy modules that cover the attachment member where the reciprocating attachment is seated. Therefore, the connected ring module can be used in conjunction with the reciprocating attachment or without the reciprocating attachment (e.g., with the attachment removed), so the outer surface of the ring module can be placed against the user's skin, if necessary for the type of treatment being administered.

In another embodiment, the LEDs and/or one or more of any of the other treatments or discussed herein (e.g., microcurrent, temperature, cleansing, etc.) can be part of the vibration therapy device and not removable. In a preferred embodiment, the control center or user interface includes an up button, a down button and a select button, which can be used for scrolling or toggling through various modes, going up or down in intensity or mode and selecting the modes or modules or turning different functions (vibration, light, micro-current, etc.) on or off.

It will be appreciated that the vibration therapy device together with the therapy module and reciprocating attachment may be referred to herein as a vibration therapy system.

In a preferred embodiment, the light ring module (or other ring module) includes alignment or securement recesses defined in a rear side thereof that receive the securement protrusions. Magnet members are positioned in the ring and adjacent the securement recesses. It will be appreciated that the magnet members associated with the securement recesses are magnetically attracted to the securement protrusions.

In a preferred embodiment, the motor is preferably attached to a motor mount bracket that secures the motor to the housing. Preferably, the motor mount bracket includes a middle member having first and second opposite sides. The motor is positioned on the first side and the eccentric weight is positioned on the second side of the middle member. The push rod assembly comprises an L-shaped or curved connector or push rod (connected to the eccentric weight) and the reciprocating shaft (with pivotal connections therebetween). The middle member includes a shaft opening defined therein. The motor includes a rotatable motor shaft extending therefrom that extends from the first side of the middle member, through the shaft opening and to the second side of the middle member. In a preferred embodiment, the motor mount bracket includes a battery bracket portion extending therefrom that secures the battery in place.

Generally, when the therapy module is attached, the head portion of the vibration therapy device includes two concentric attachment rings, the inner one for the reciprocation or massage attachment (e.g., silicone vibration head) and the outer one for the therapy modules (e.g., LED, Micro-current etc.). In a preferred embodiment, the male attachment also includes magnets for attachment (or similar attachment mechanism) and can also include an electrical connection similar to the outer ring. Therefore, a single attachment that covers both the outer and inner part can be used that attaches to male attachment and securement protrusions, for example to accommodate more LEDs.

In another preferred embodiment, the reciprocating attachment can includes hooks for securing a microfiber material on the reciprocating attachment that can be used on the user's face or other body part for the vibration therapy treatment. The microfiber material is secured on both sides and under the reciprocating attachment and stretches across the top contact surface of the reciprocating attachment. The microfiber material can include lotion therein for treating the persons' skin.

It will be appreciated that different types of massage or reciprocating attachments can be used on the vibration therapy device. As discussed herein, one or more of the reciprocating attachments can include a groove extending therearound for attachment of a treatment member (for treating the user's skin). Another massage attachment can include a cone portion or be cone shaped. Another massage attachment can include a soft portion and a harder portion that are connected by velcro. Another massage attachment can include a plurality of spikes or needles that provide a microneedling type treatment.

The present invention is a handheld device that helps to reduce tension, relax facial muscles, and achieve healthier-looking skin by gently stimulating the face. The system includes microcurrent, blue, red, and red+infrared light LED, and cleansing treatments, allowing a user to customize their facial therapy in one easy-to-use versatile device. The variety of treatment rings can be used to help lift, tone, rejuvenate, and deep clean.

It will be appreciated by those of skill in the art that percussive therapy is the rapid and repetitive application of pressure perpendicular to the body. The percussive stimulus of the device causes the targeted tissues to experience both pressure and vibration stimuli simultaneously. We know that these stimuli have therapeutic benefits related to reduced tension, pain relief, and increased circulation. The percussive therapy of the present invention has been optimized for the face through a reduced amplitude (compared to the prior art).

Photobiomodulation (PBM), also referred to as "phototherapy" or "light therapy", utilizes non-ionizing forms of light sources including LASERS, LEDs, and broadband light, in the visible and near-infrared spectrum. This non-thermal process (no heat) allows light energy to penetrate the skin leading to changes at the molecular, cellular, and tissue levels of the body. LED (light emitting diode) therapy is a skincare treatment for several conditions that uses varying wavelengths of light, including red and blue, to stimulate the skin and tissue beneath. In a preferred embodiment, the red light has a wavelength of 633 nm±10 nm and a power density of 78±5%. Red light is intended to reduce periorbital wrinkles (the wrinkles around the eyes). In a preferred embodiment, the blue light has a wavelength of 415 nm±10 nm and a power density of 50±5%. Blue Light is intended to reduce mild to moderate acne. In a preferred embodiment, the red+infrared light has wavelengths of 633±10 nm/830 nm±10 nm and power densities of 78±5%/55±5%. Red+ infrared light therapy is intended to provide therapeutic warming to temporarily reduce pain and discomfort and is intended to reduce periorbital wrinkles (the wrinkles around the eyes).

Microcurrent therapy utilizes low-level electrical voltage to stimulate muscles, primarily of the face. This stimulation acts as a workout that often results in the temporary tightening, toning, or contouring of the targeted muscles which often leads to the appearance of reduced wrinkles, especially on the forehead region. In a preferred embodiment, the present invention provides microcurrent with a pulsed biphasic waveform, a pulse frequency of 8 Hz and settings of 11 µA, 300 µA, 500 µA. In use, the microcurrent firms and tightens the skin and improves muscle tone and contour in the face/neck. The microcurrent therapy module can be used with a conductive gel.

Cryotherapy or cold therapy, is a process where the body is exposed to low temperatures for therapeutic purposes, resulting in the reduction of blood flow to a particular area leading to decreased local tissue temperatures, and/or the regulation of gene expression. While this is commonly done through the use of liquid nitrogen or ice for full body cryotherapy, local cryotherapy is able to be achieved through a battery-powered device via a process called thermoelectric cooling. In a preferred embodiment, the cold ring or cryotherapy may be provided at three different temperatures (i.e., the user can toggle between temperatures using controls). Preferably, the temperatures are 26° C./78° F., 22° C./71° F. and 18° C./65° F. Cold therapy is intended to decrease pain, decreases muscle spasms, and decrease inflammation.

Thermotherapy or heat therapy, is a process where the body is exposed to high temperatures for therapeutic purposes, resulting in increased blood flow to a particular area leading to increased local tissue temperatures. Local thermotherapy is able to be achieved through a battery-powered device via a process called thermoelectric heating. In a preferred embodiment, the heat ring or thermotherapy may be provided at three different temperatures (i.e., the user can toggle between temperatures using controls). Preferably, the temperatures are 35° C./95° F., 39° C./102° F., 43° C./109° F. Heat therapy is intended to decrease pain, decrease muscle spasms, decreases tension, and increases blood flow.

The inventive device and system may provide any or all of the treatment discussed herein, such as percussive or vibration therapy, PBM, light therapy, microcurrent therapy, cryotherapy and/or thermotherapy.

In a preferred embodiment, the massage attachment is secured to the vibration therapy device via magnets. Preferably, a magnet is included in the massage attachment and a complementary magnet is included in the attachment member. It will be appreciated that the low amplitude of about 3.0 mm allows the magnetic connection between the magnet in the attachment member on the end of the push rod assembly to remain secured in place during reciprocation and use of the device. With a higher amplitude (or linear velocity), the massage attachment may disconnect during use. The amplitude combined with the frequencies or speeds discussed herein allows for magnetic securement of the attachment member. Therefore, it will be appreciated by those of ordinary skill in the art that the about 3.0 mm amplitude coupled with the frequencies of 1750 ppm, 2100 ppm and 2400 ppm provides beneficial results when used on the face, as described herein, and allows the magnetically connected attachment member to be secured to the end of the push rod assembly.

An amplitude as low as 0.5 mm provides a vibrating stimulus when used on the face. The inventors have determined that 3.0 mm provides beneficial results. This amplitude, combined with the different attachments (shape and density), was found to be comfortable, but also provides a relative intensity for the face. Therefore, this percussive force is optimized for use on the delicate features of the face.

In a preferred embodiment, the present invention provides dual therapies simultaneously, the first being percussion and the other being LED light therapy, hot or cold therapy or others discussed herein. It will be appreciated that the percussion therapy can also be varied based on the type of massage attachment (e.g., micropoint) that is secured to the end of the push rod assembly.

In a preferred embodiment, the vibration therapy device includes a waterproofing feature for preventing moisture from getting in through where the push rod assembly extends outside of the housing. Preferably, a sleeve (e.g., a silicone sleeve) surrounds the portion of the reciprocating shaft that extends outside of the housing so that it is not exposed. The sleeve is secured within the attachment member at one end and inside the protrusive portion of the housing on the other end. The sleeve is secured at both ends and can flex or move as the reciprocating shaft reciprocates. This provides water resistance to the device.

Other therapy modules are within the scope of the present invention. For example, one type of therapy modules may include an LED module that is a cap module and does not include a central opening for percussion. Another therapy module may include one or more skin scanning sensors that can be used for oil detection and/or moisture detection associated with the user's skin. Other therapy modules may include ultrasound or ultrasonic facial treatment or radio frequency treatment for facial rejuvenation. The radio frequency module can be used to help with skin tightness and wrinkles. The ultrasonic module can be used to help with lymphatic drainage, blood flow and muscle toning. The scanning module can be used to detect moisture and oil levels and to personalize protocols and track progress. All of these modules can be either ring modules or cap modules and can be configured the same as or similar to any of the other therapy modules disclosed herein.

It will be appreciated that all components and feature on the different embodiments shown herein are interchangeable with the components and features of any of the other embodiments discloses herein.

BRIEF DESCRIPTION OF THE DRAWINGS

Like numerals refer to like parts throughout the several views of the drawings.

DETAILED DESCRIPTION OF THE PREFERRED EMBODIMENTS

Figure 1:
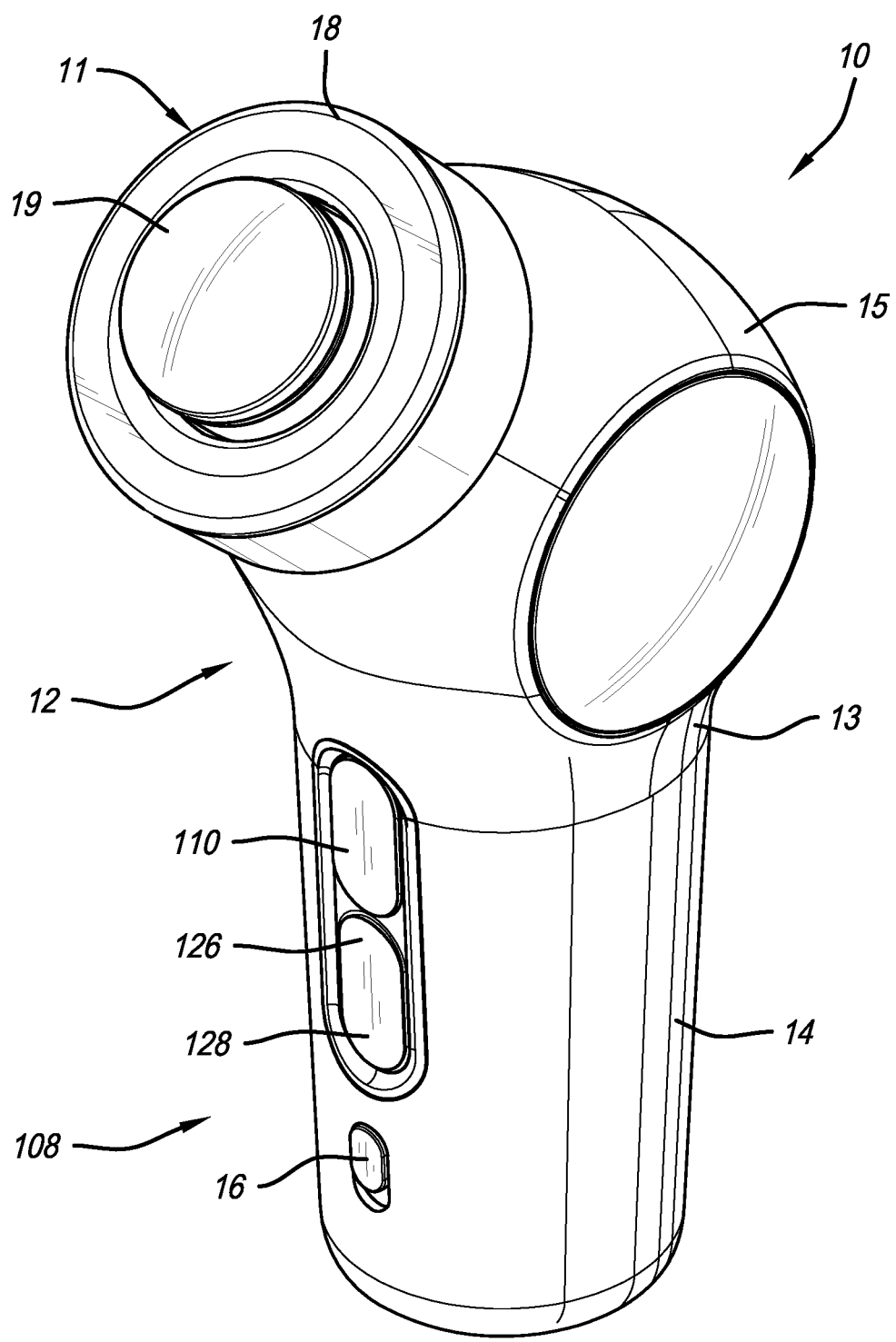
FIG. 1 is a perspective view of a vibration therapy system and device in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments. If a component is not shown in a drawing then this provides support for a negative limitation in the claims stating that that component is "not" present. However, the above statement is not limiting and in another embodiment, the missing component can be included in a claimed embodiment.

Reference in this specification to "one embodiment," "an embodiment," "a preferred embodiment" or any other phrase mentioning the word "embodiment" means that a particular feature, structure, or characteristic described in connection with the embodiment is included in at least one embodiment of the-disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms.

The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

Referring now to the drawings, which are for purposes of illustrating the present invention and not for purposes of limiting the same, the drawings show a vibration therapy system 10 that includes a vibration therapy device 12, one or more reciprocating attachments 19 and one or more therapy modules 11. The reciprocating attachments can have different shapes. The therapy modules 11 can have different shapes and include different types of therapy, such as light, micro-current, heat, cold, vibration, etc.

Figure 2:
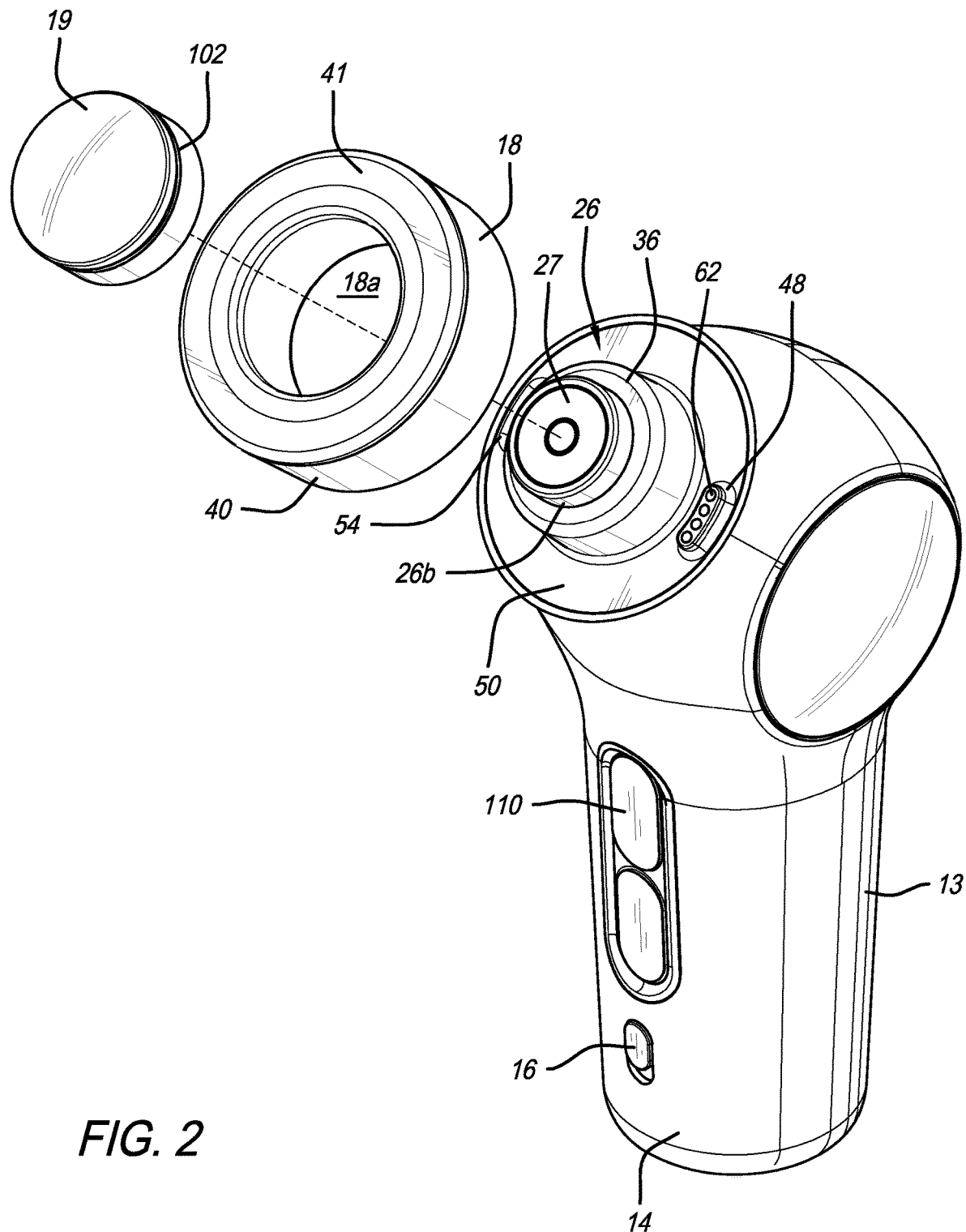
FIG. 2 is a perspective view of the vibration therapy device with the therapy module and reciprocating attachment exploded therefrom.
Figure 3:
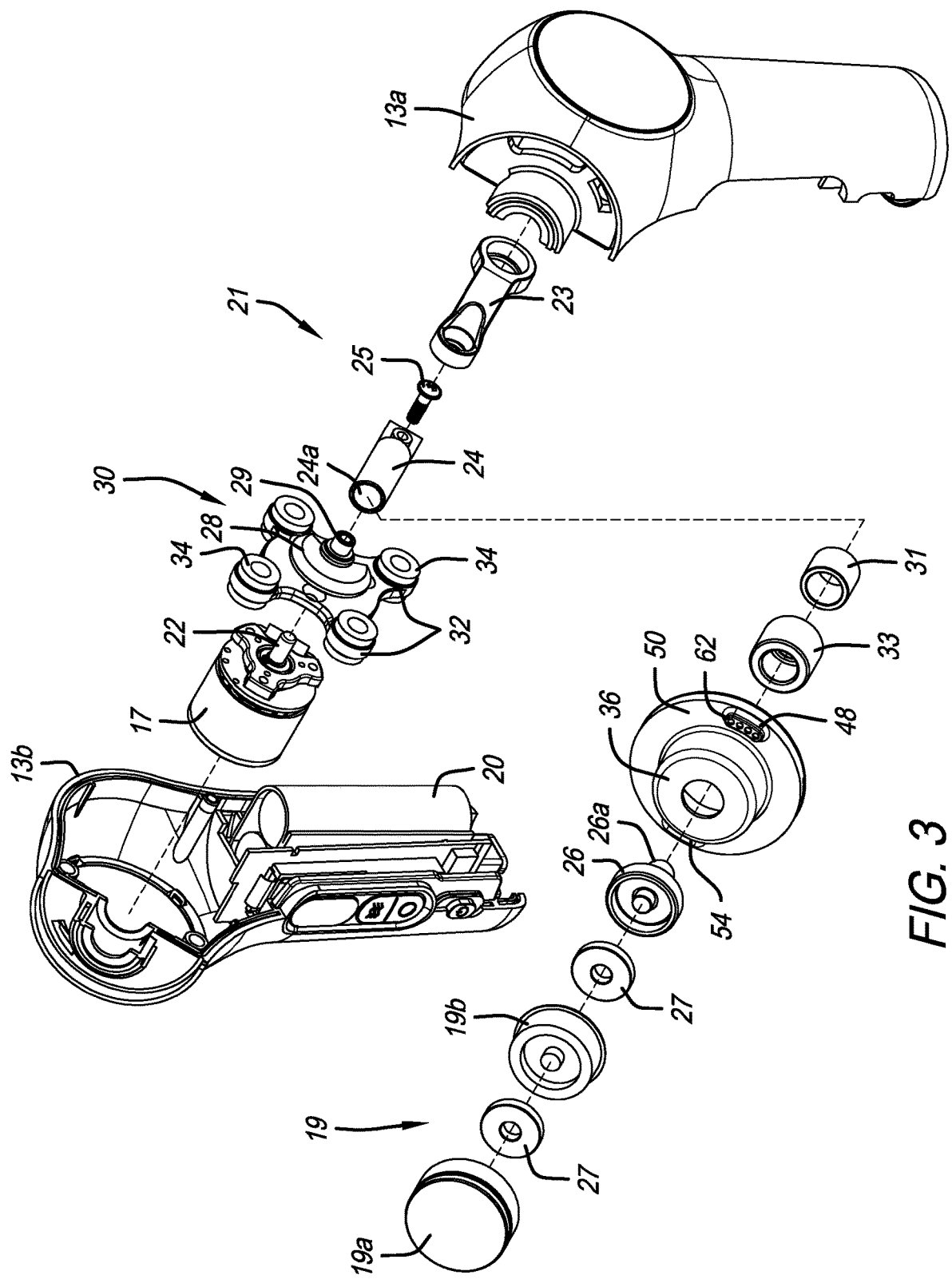
FIG. 3 is an exploded view of the vibration therapy device.

As shown in FIGS. 1-3, generally the vibration therapy device includes a housing 13 (two housing halves 13a and 13b are shown in FIG. 3), a handle portion 14, a head portion 15 and a switch 16 for activating the motor 17. FIGS. 1-8 show the vibration therapy device 12 with a therapy module 11 that is referred to herein as a ring module 18 (due to its shape with a central opening 18a) and a reciprocating attachment 19. As shown in FIG. 3, in a preferred embodiment, the vibration therapy device 12 includes an electrical source, such as a battery 20, positioned in the handle portion 14, the motor 17 positioned in the head portion 15, and a push rod assembly 21 operatively connected to the motor 17 and configured to reciprocate in response to activation of the motor 17.

Figure 4:
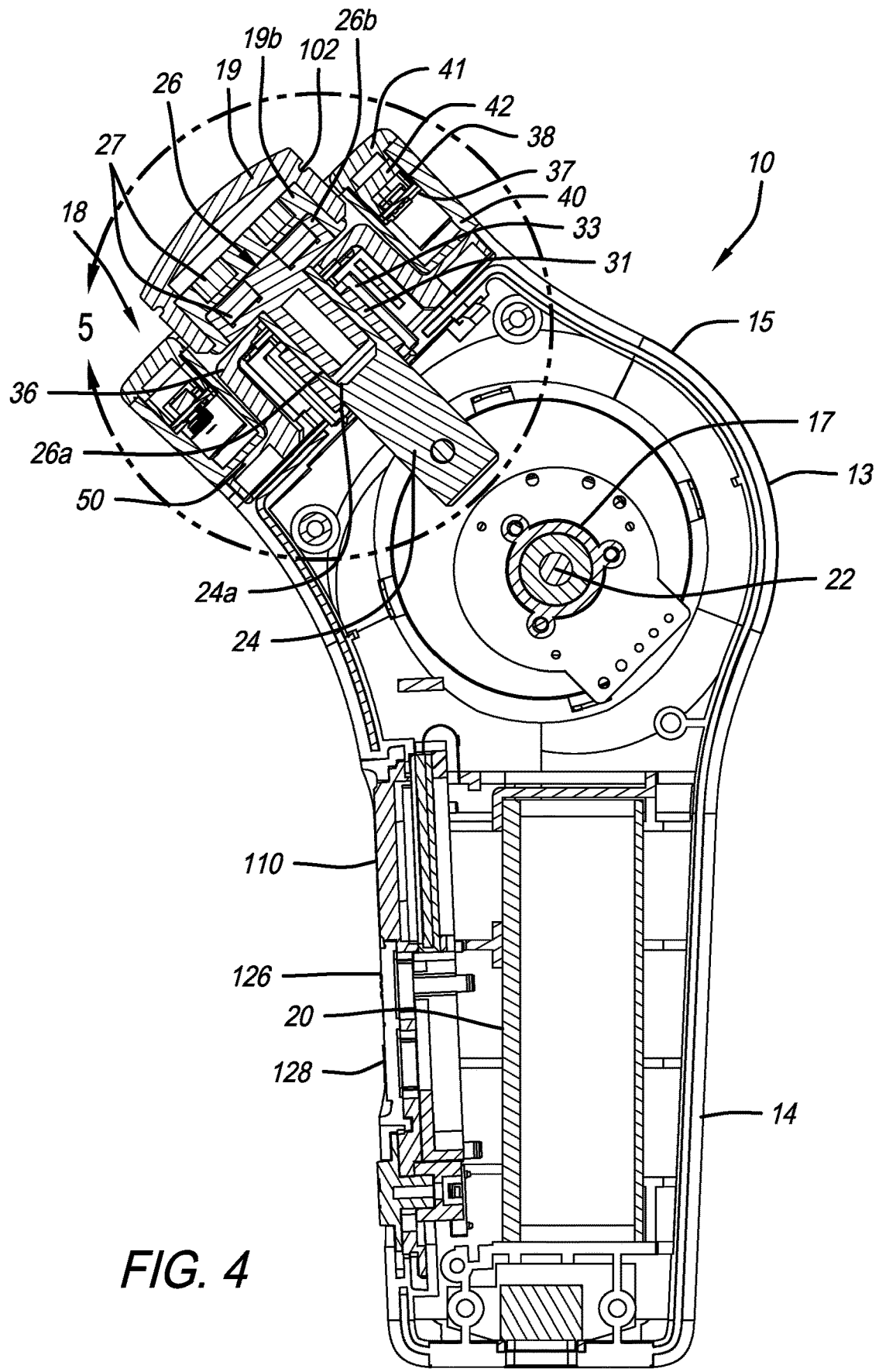
FIG. 4 is a cross-sectional view of the vibration therapy device.
Figure 5:
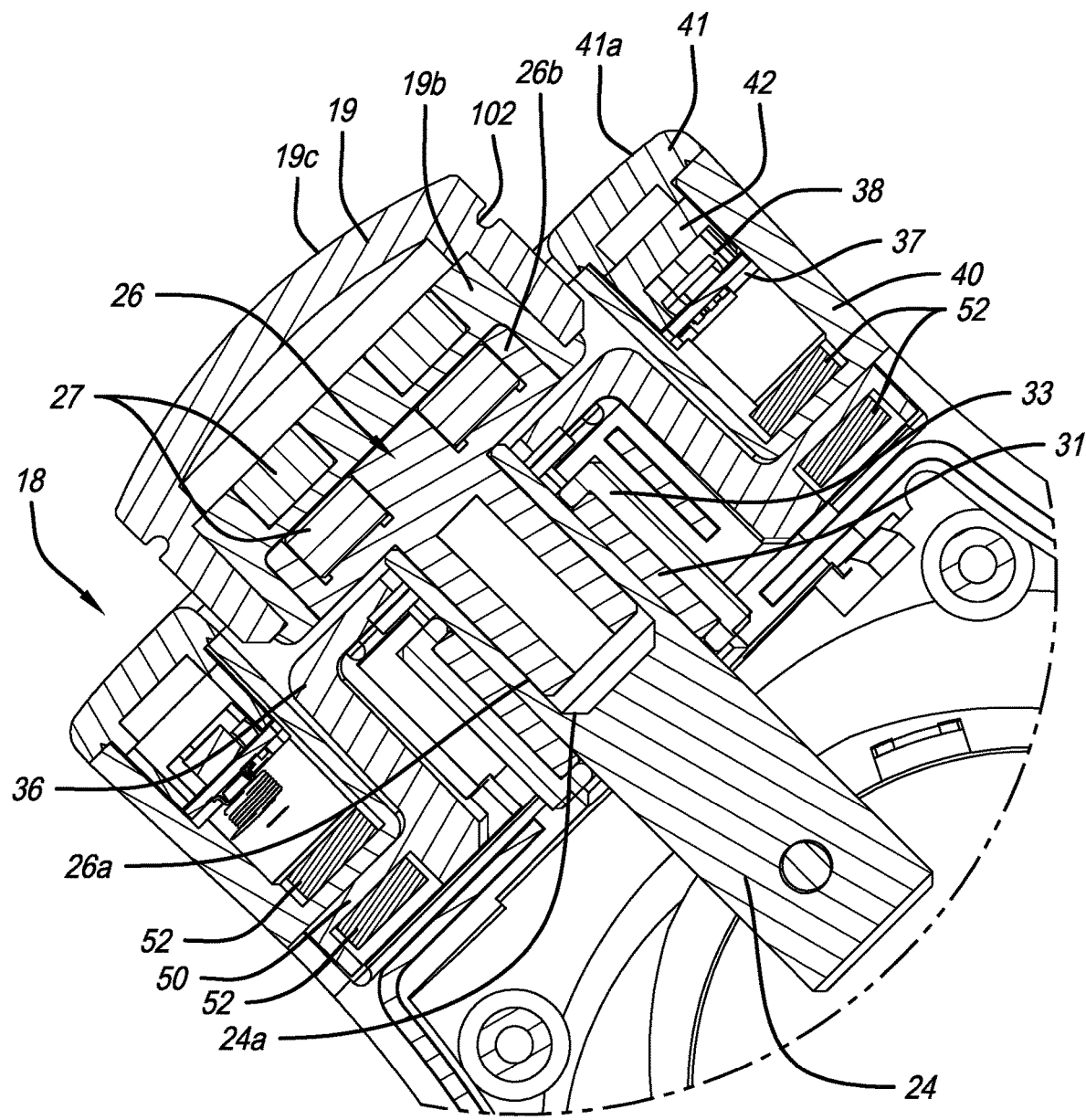
FIG. 5 is a cross-sectional view of a portion of the vibration therapy device taken along 5-5 of FIG. 4.

In a preferred embodiment, the rotation of the motor shaft 22 is converted to reciprocating motion of the push rod assembly 21. It will be appreciated that the push rod assembly includes any set of components for converting the rotation motion of the motor to reciprocating motion of the massage or reciprocating attachment. As shown in FIGS. 3-5, in a preferred embodiment, the push rod assembly 21 includes a push rod 23 that is pivotably connected to a reciprocating shaft 24 (see pivot pin 25), and an attachment member 26 that is operatively connected to the reciprocating shaft 24. In a preferred embodiment, the shaft 26a of the attachment member extends into and is connected within (via threads, friction fit, interference fit, etc.) an opening 24a defined in the reciprocating shaft 24. The distal end of the attachment member 26 (which is also the distal end of the push rod assembly 21) removably receives the reciprocating attachment 19. It will be appreciated that the term push rod assembly used herein includes any of the drive train components discussed herein or combinations thereof, e.g., push rod 23, reciprocating shaft 24 and attachment member 26 or the like that provide reciprocating motion and include the reciprocating attachment on the distal end thereof. The push rod assembly also includes the attachment member 26 (and any related components, such as the magnet described below) or any other connector at the end of the reciprocating components that allows connection of a reciprocating attachment to be used for massage or therapy.

Preferably, the drive train also includes a counterweight member 28 between the motor shaft 22 and the push rod 23. The motor shaft 22 is received in an opening in the counterweight member 28 and an offset shaft 29 extends from the counterweight member 28 and is received in an opening in the push rod 23. The reciprocating shaft 24 extends through the bush 31 and bush holding structure 33.

In a preferred embodiment, the motor 17 is secured to a motor mount 30 that includes a plurality of feet 32 that are secured to the housing 13 via threaded fasteners or the like that extend through openings in the feet 32. Dampening rings 34 and dampening washers can also be included. All dampening components herein are made of rubber, silicone or the like and are provided to prevent plastic to plastic or plastic to metal contact and to reduce noise and vibration.

In a preferred embodiment, the attachment member 26 includes the shaft 26a and a magnet seat 26b. The magnet seat 26b includes a magnet 27 received therein or otherwise operatively associated therewith. As shown in FIG. 3, the housing 13 includes a cap portion 35 that includes the module seat 50 and a protrusive portion 36. The attachment member 26 extends through an opening in the cap portion such that the magnet seat 26b is located outside of the housing 13, and particularly, the protrusive portion 36 of the housing 13. As described above, The distal end of the attachment member 26 (the magnet seat 26b) removably receives the reciprocating attachment 19. In a preferred embodiment, the magnet 27 in the attachment member is magnetically attracted to a magnet 27 in the reciprocating attachment 19 or other component placed on the attachment member 26. FIG. 3 shows an exemplary reciprocating attachment 19 including the main body portion 19a, inner support portion 19b and magnet 27.

Figure 6:
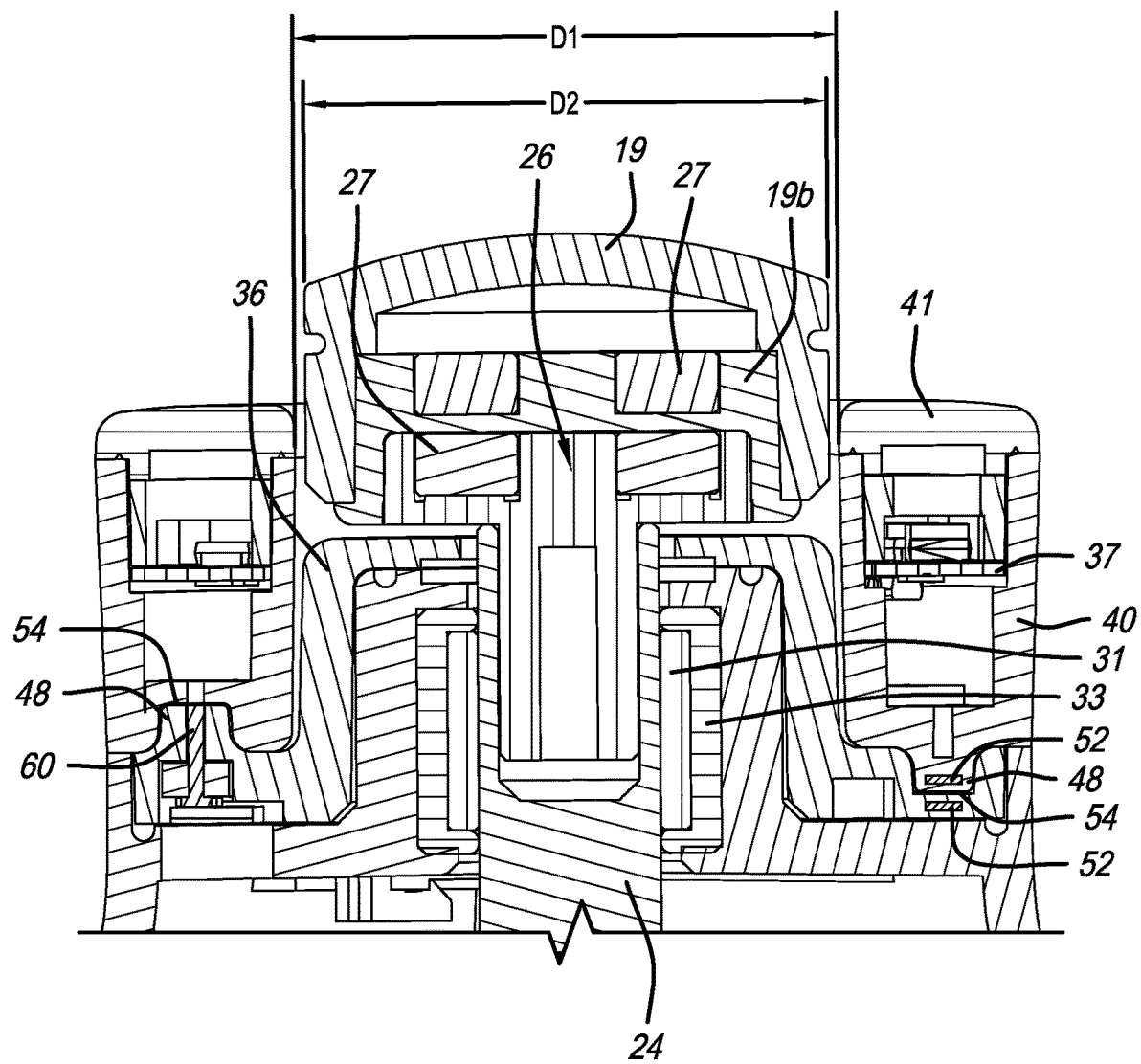
FIG. 6 is a cross-sectional view of a portion of the vibration therapy device showing the securement protrusions and securement recesses with the electrical connection and magnetic connection.

As shown in FIG. 2, in a preferred embodiment, the head portion 15 includes a module seat 50 that removably receives the therapy modules 11. As shown in FIG. 6, the vibration therapy system 10 includes an attachment system 44 for properly aligning or mounting and attaching or securing the various therapy modules 11 on the module seat 50, as well as providing electrical connection or communication (if needed) between the therapy modules 11 and the vibration therapy device 12. In a preferred embodiment, the attachment system 44 includes magnetic attraction between the module seat 50 and therapy module 11 and includes one or more complementary securement protrusions 48 and securement recesses 54 extending or protruding from the module seat 50 and/or the back of the therapy module 11. The securement protrusions are received in the securement recesses. The attachment system 44 provides the ability to accommodate the swappable or interchangeable therapy modules 11 (e.g., ring module 18) with different facial treatment technologies. FIG. 6 also shows the central opening diameter D1 of the central opening 18a of the ring module 18 and the reciprocating attachment diameter D2 of the reciprocating attachment 19. As shown, the central opening diameter D1 is larger than the reciprocating attachment diameter D2, such that the reciprocating attachment 19 is configured to reciprocate within and relative to the ring module 18.

Figure 7:
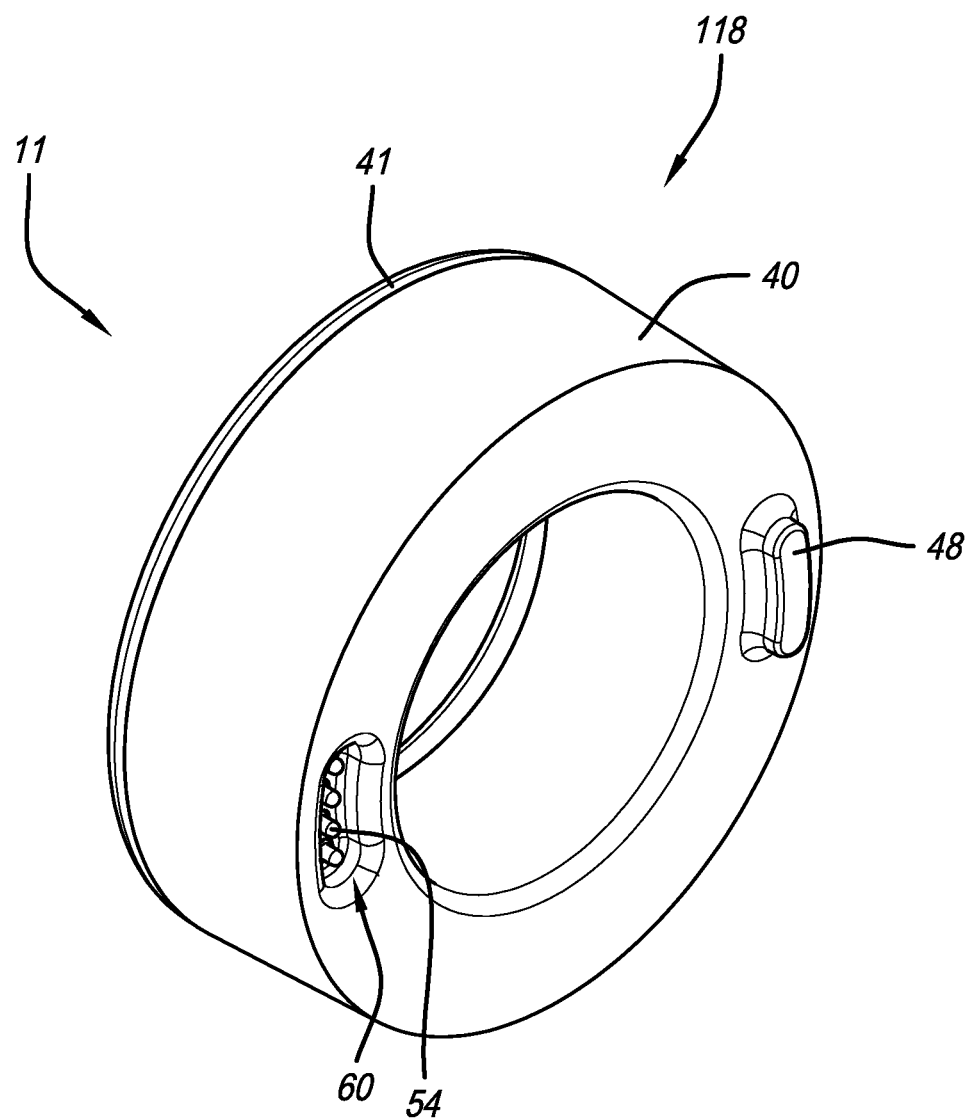
FIG. 7 is a rear perspective view of the light ring module.

As shown in FIGS. 6-7, in a preferred embodiment, one securement protrusion 48 extends from the back of the therapy module 11 and one securement recess 54 is defined in the module seat 50. Also, one securement recess 54 is defined in the back of the therapy module 11 and one securement protrusion extends from the module seat 50. In a preferred embodiment, at least one of the securement protrusions and at least one of the securement recess include one or more magnet members 52 associated therewith that are magnetically attracted to one another, that help secure the ring module 18 (or other therapy module 11) onto the module seat 50 and the vibration therapy device 12. One, two or more magnet members can be included. The magnet members 52 are located within the housing of the therapy module (see, e.g., FIGS. 5 and 2) and within the housing of the head portion and adjacent to or below the module seat 50 (see, e.g., FIGS. 5 and 19). Sets of complementary magnets 52 may be positioned around the base of the therapy module 11 and the module seat 50. For example, in a preferred embodiment, the module seat 50 includes a first set of six magnets 52 associated therewith and each therapy module 11 includes a second set of magnets 52 associated therewith that are magnetically attracted to the first set of magnets in or associated with the module seat 50. A set can be any number of magnets between 1-25.

In a preferred embodiment, the system includes an electrical connection system 58 between the vibration therapy device 12 and the therapy module 11. In a preferred embodiment, the therapy module 11 includes male electrical contacts 60 extending therefrom (see FIGS. 6 and 10) and the module seat 50 includes complementary female electrical contacts 62. Power is supplied from the battery 20, through the male and female electrical contacts and to the LEDs or other powered components. It will be appreciated that the male and female electrical contacts can be reversed. In a preferred embodiment, the male or female electrical contacts are associated with one of the securement recesses 54 and one of the securement protrusions 48. In the embodiment shown in the drawings, the securement protrusion 48 that extends from the back of the therapy module 11 is a magnetic securement protrusion and the securement recess 54 that is defined in the module seat 50 is a magnetic securement recess. Furthermore, the securement recess 54 that is defined in the back of the therapy module 11 is an electrical securement recess (and includes male electrical contacts) and the securement protrusion 48 that extends from the module seat 50 is an electrical securement protrusion (and includes female electrical contacts).

As shown in FIG. 1, in a preferred embodiment, the handle portion 14 forms an angle of about 120 degrees with the reciprocating shaft 24 to avoid blocking the user's view during treatment. Anywhere between 90 degrees and 180 degrees is within the scope of the invention. In another embodiment, the head portion can be rotatable and/or pivotable and/or swivelable with respect to the handle portion 14.

Figure 8:
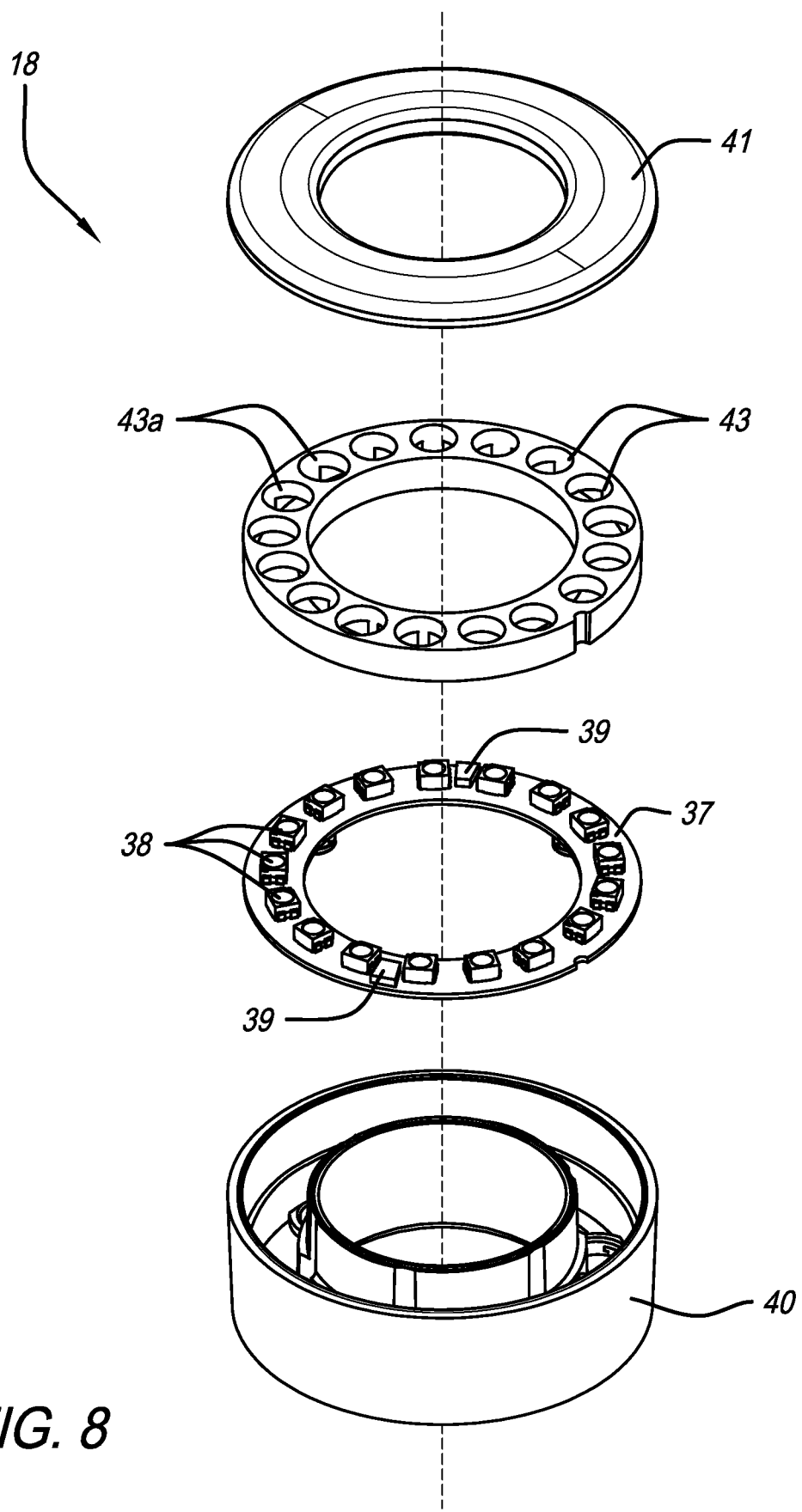
FIG. 8 is an exploded perspective view of the light ring module.

FIG. 8 shows the components of the light ring module 18 including the printed circuit board 37 including the LEDs 38 and proximity sensors 39. In a preferred embodiment, the proximity sensors 39 are positioned approximately 180° from another. With respect to 180°, approximately means within 10°. However, they can be positioned anywhere around the ring. The proximity sensors 39 are provided so that LED lights in the light module only turn on (or go from dimmed to "treatment level" or off to "treatment level") when they are less than a predetermined distance from or the lens is in contact with the user's face or skin. In a preferred embodiment, one proximity sensor 39 is located at about twelve o'clock on the PCB and the other is located at about six o'clock. In use, after activating the light ring module, the lights remain off or in a dimmed state until the front surface of the module is placed within a predetermined distance of the user's face, at which point the lights brighten to a treatment level (where the lights will be effective for the desired treatment—e.g., red LED treatment, blue LED treatment or infrared). Preferably, the proximity sensors are programmed such that they only determine the proximity at intervals or at a predetermined frequency (e.g., every one second) so that the lights are not turning on and off every time the device is pulled away from the face or angled during use on the face such that the proximity sensor is out of range. Any type of proximity sensor can be used. In a preferred embodiment, the proximity sensor emits a beam that is reflected by the user's face. The sensor determines the distance with the face based on the time (or frequency) for the beam returning from the user's skin after reflection. It will be appreciated that by having two proximity sensors 180° apart, as long as one is within the predetermined range of distance from the skin (operating surface), the lights will not dim or turn off (or go to a point that is less than the desired treatment level or intensity of the lights).

As shown in FIG. 8, in a preferred embodiment, the light ring module includes a housing portion 40, PCB 37, cover or lens 41 and a light direction member 42 that includes a plurality of openings 43 defined therein. The openings 43 are each aligned with an LED 38 and provide a tunnel so that the light beams emitted from each of the LEDs are directed generally parallel to one another and, therefore, generally perpendicular to the cover 41 and the user's skin as the device is used. This helps prevent the light from shining outwardly and into the user's eyes during use. The ring module includes the central opening 18a and an outer surface 41a. As shown in FIG. 5, in a preferred embodiment, the contact surface 19c of the reciprocating attachment 19 extends further from the module seat 50 than the outer surface 41a of the ring module 18. Other types of ring modules with other therapies are in the scope of the present invention.

Figure 9:
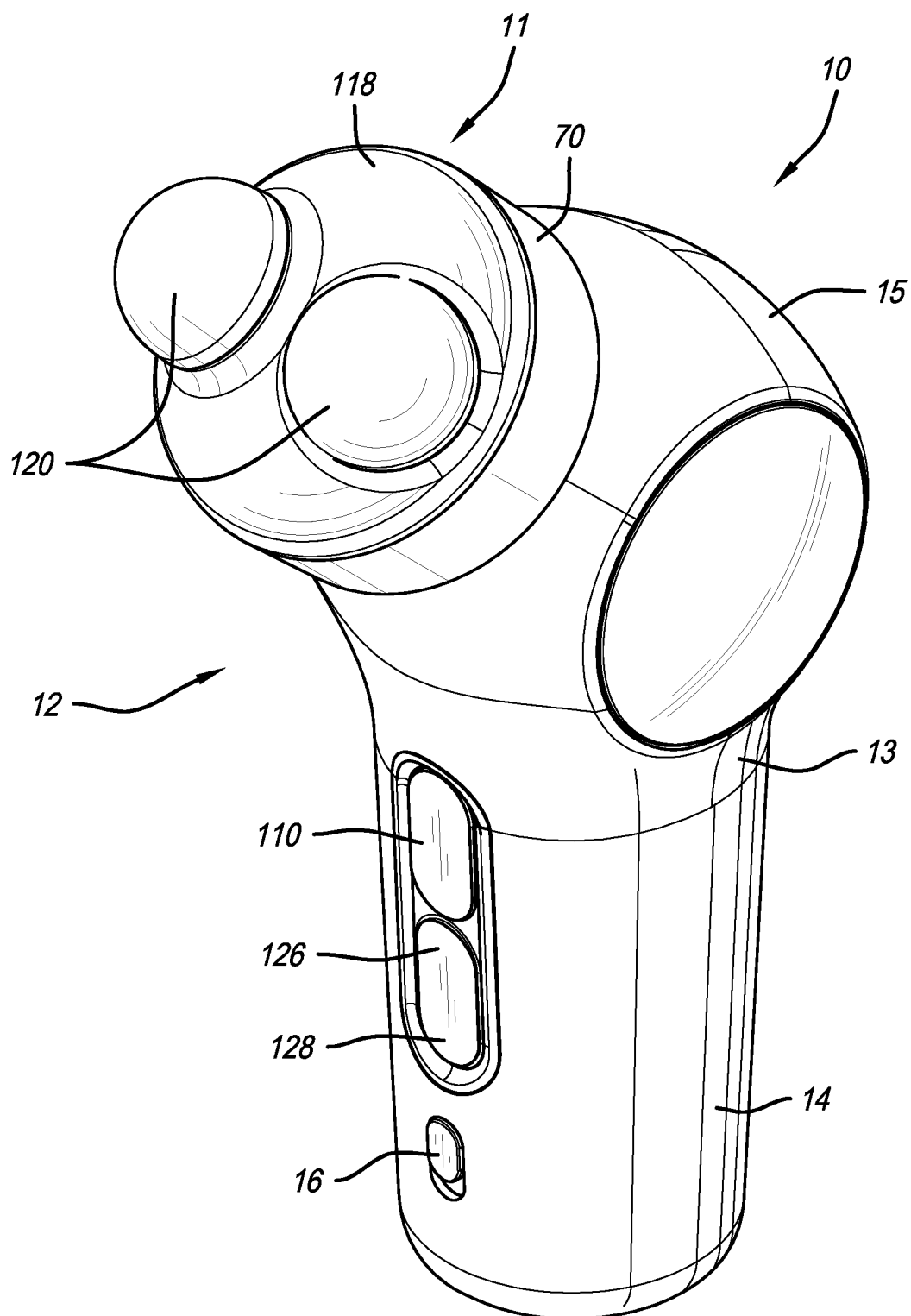
FIG. 9 is a perspective view of the vibration therapy device with the micro-current cap module thereon.
Figure 10:
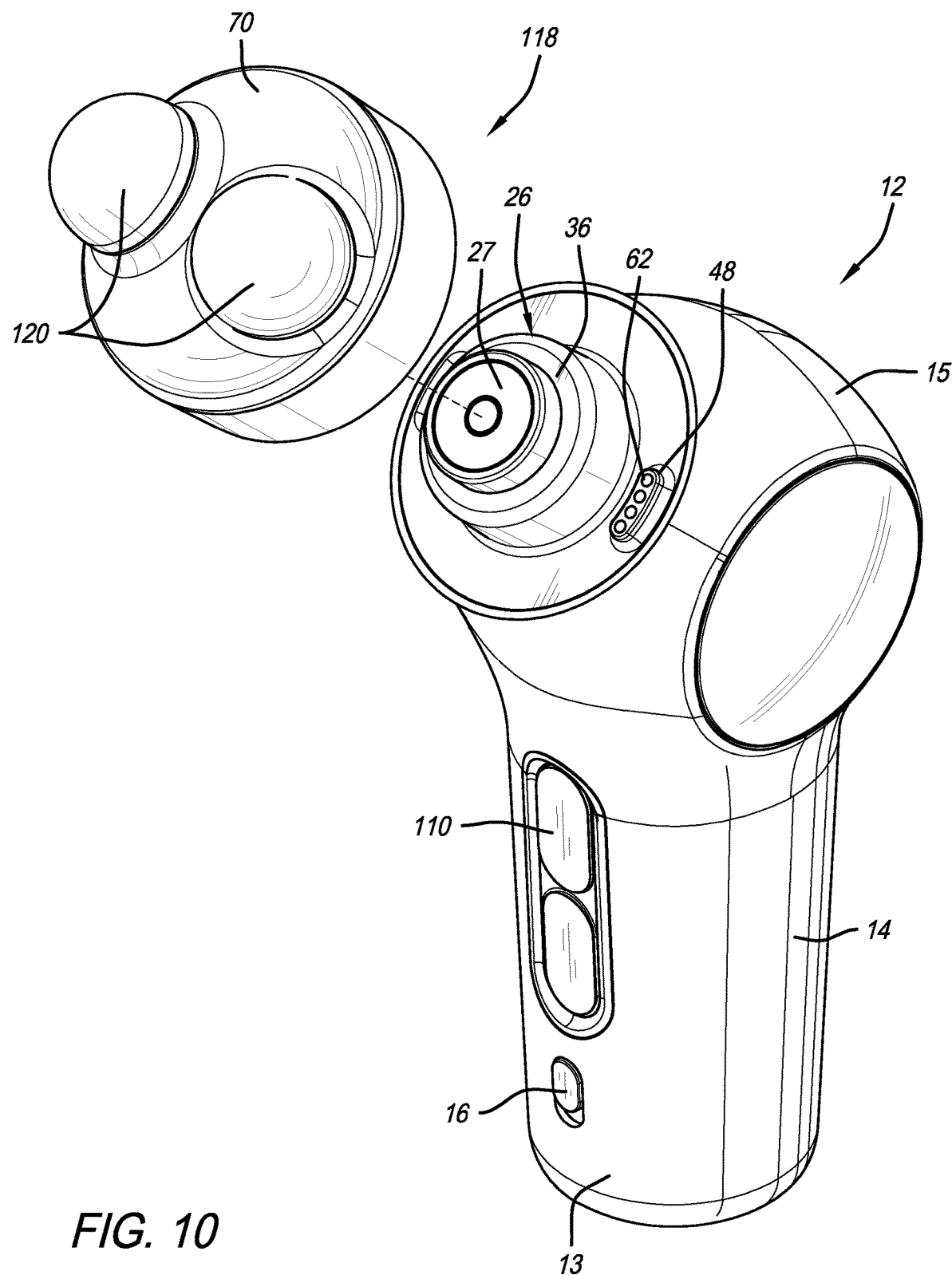
FIG. 10 is a perspective view of the vibration therapy device with the micro-current cap module exploded therefrom.
Figure 11:
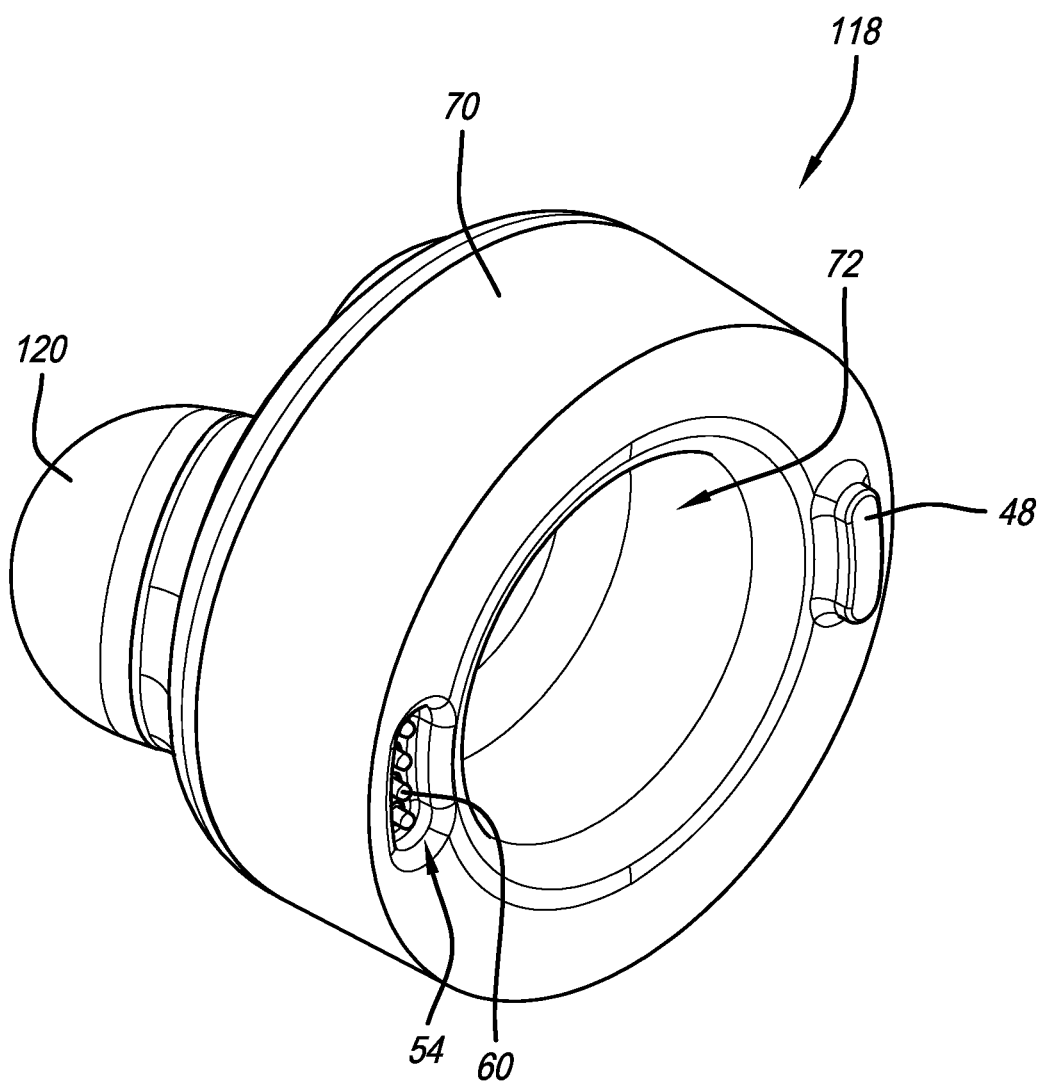
FIG. 11 is a rear perspective view of a micro-current cap module.

FIGS. 9-11 show another type of therapy module 11 referred to generally herein as a cap module and more specifically (for this particular module) as a micro-current cap module 118 that covers the magnet seat 26b of the attachment member 26. The micro-current cap module 118 includes a main body portion 70 and a rear recess 72 defined therein that receives the attachment member 26 when the micro-current cap module 118 is fitted on the module seat 50. The rear recess 72 may also be referred to herein as the central opening because regardless of the type of therapy module (cap or ring) that is received on the module seat, the attachment member 26 extends into the central opening (or rear recess). The micro-current cap module 118 shown in FIGS. 9-11 includes micro-current therapy. However, different cap modules can include other therapies. Micro-current therapy can also be included in a ring module. The micro-current cap module 118 includes first and second terminals or an anode and cathode 120. This module includes an electrical connection and magnetic attraction just like the ring module 18 described above. As will be appreciated by those of ordinary skill in the art, when the anode and cathode 120 are placed against a user's skin, an electrical connection is created and micro-current is transmitted into the user's skin to provide micro-current treatment.

Figure 12:
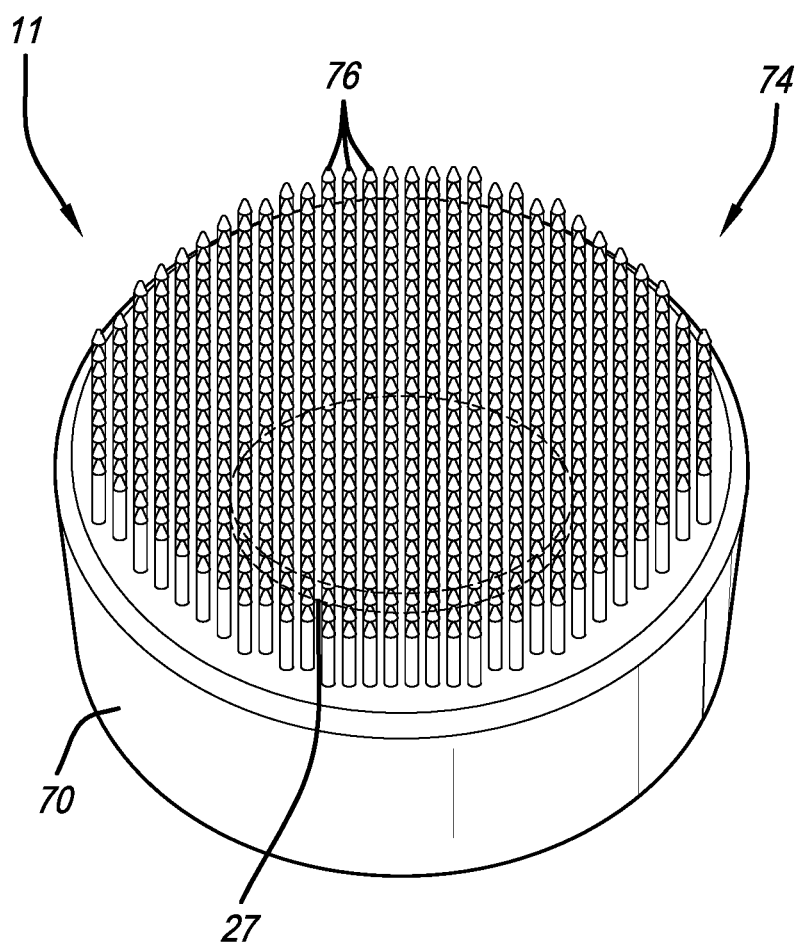
FIG. 12 is a perspective view of the cleansing attachment.
Figure 13:
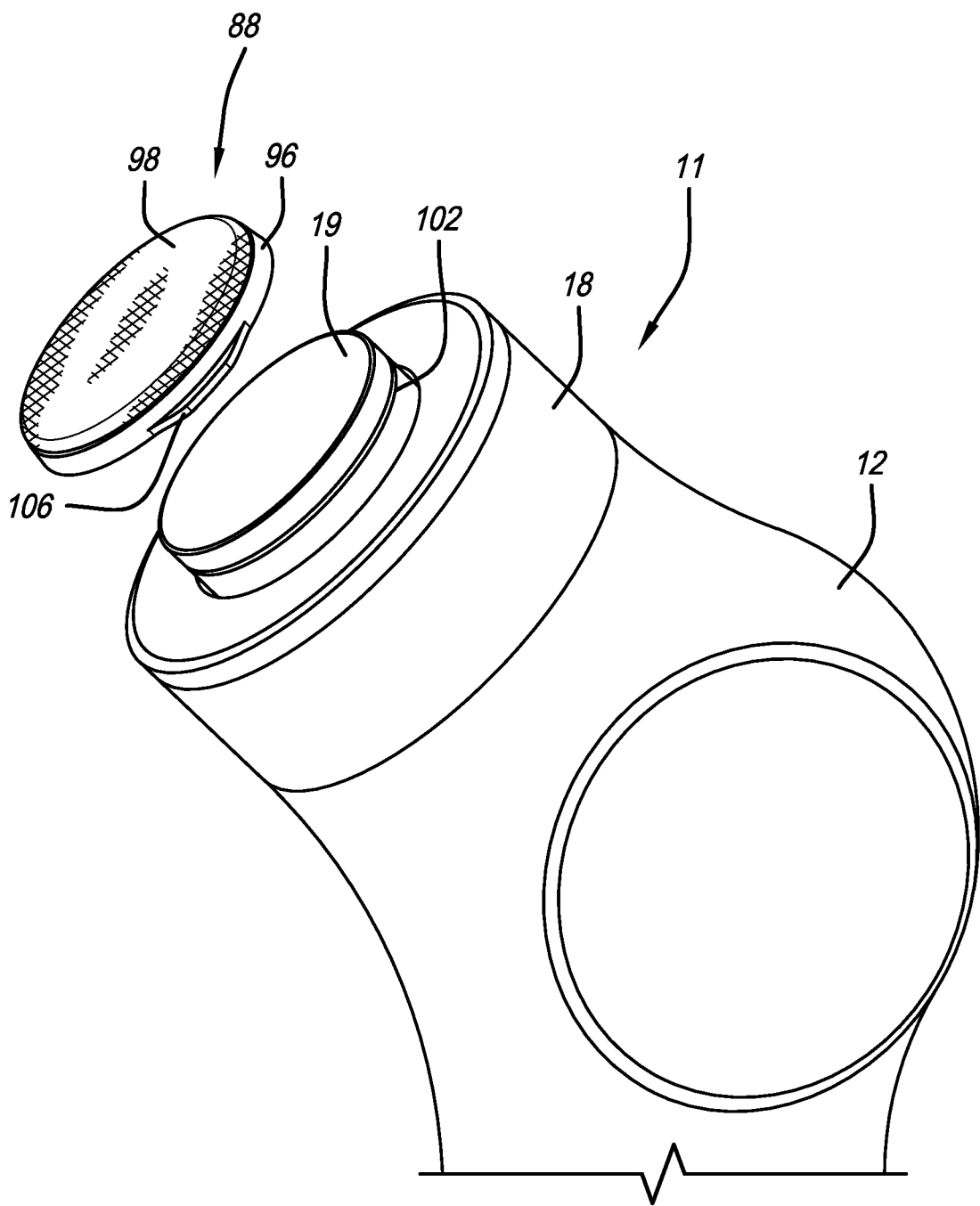
FIG. 13 is a perspective view of the vibration therapy device with a treatment member exploded therefrom.
Figure 14:
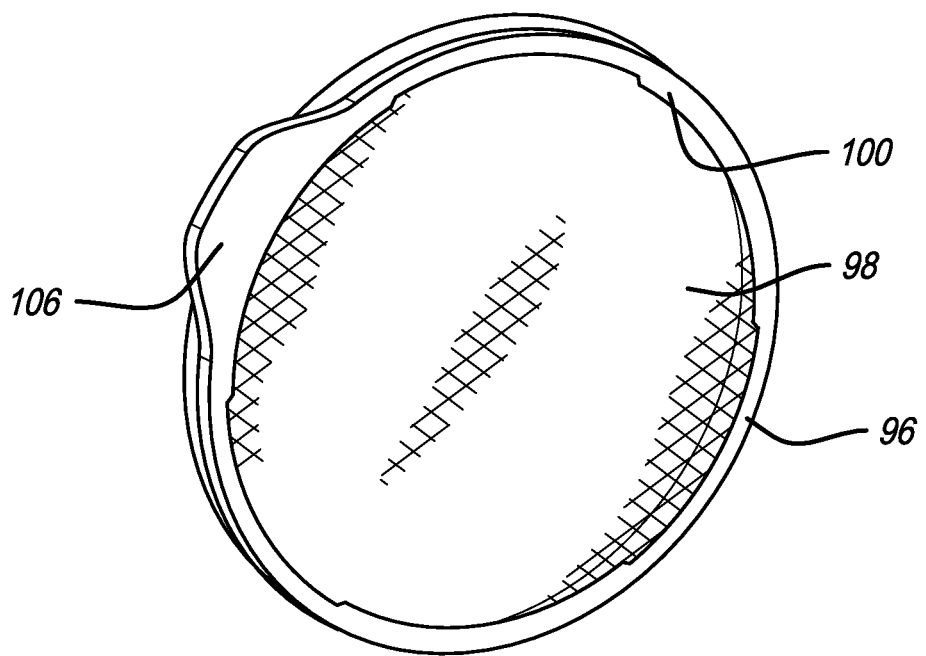
FIG. 14 is a perspective view of the therapy member.
Figure 15:
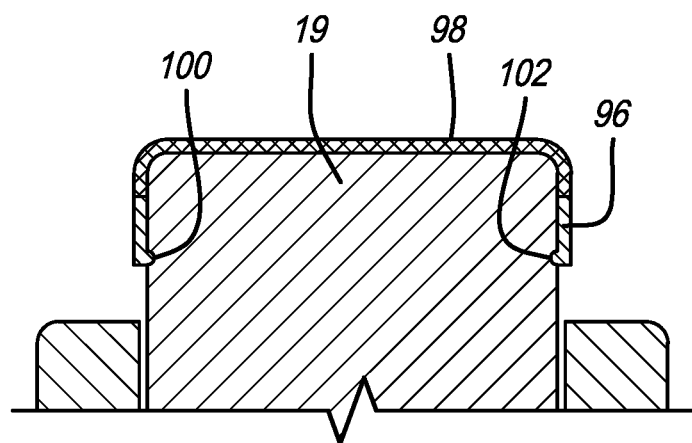
FIG. 15 is a cross-sectional view of the therapy member on the reciprocating attachment.
Figure 16:
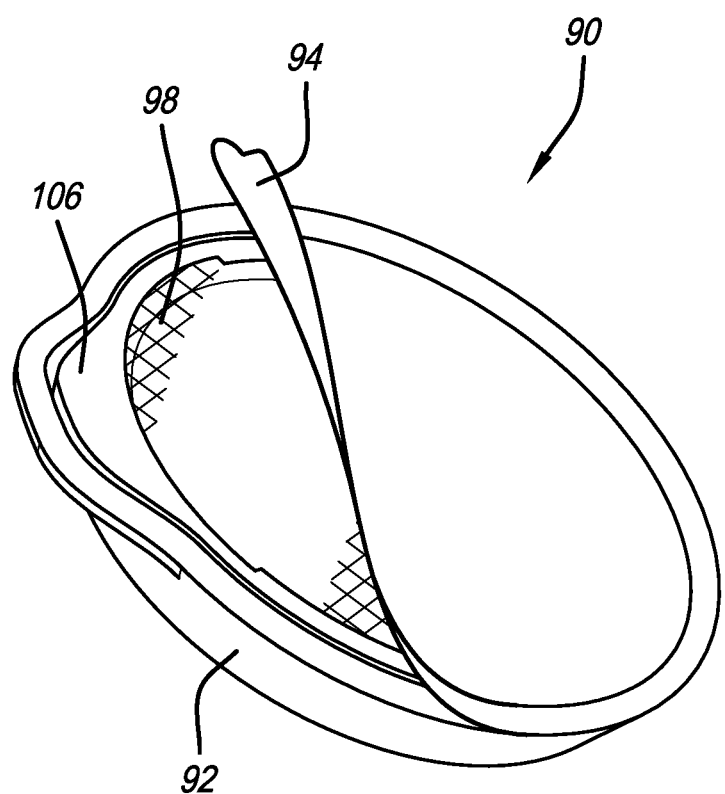
FIG. 16 is a perspective view of the therapy member in packaging with the lid partially peeled back.
Figure 21:
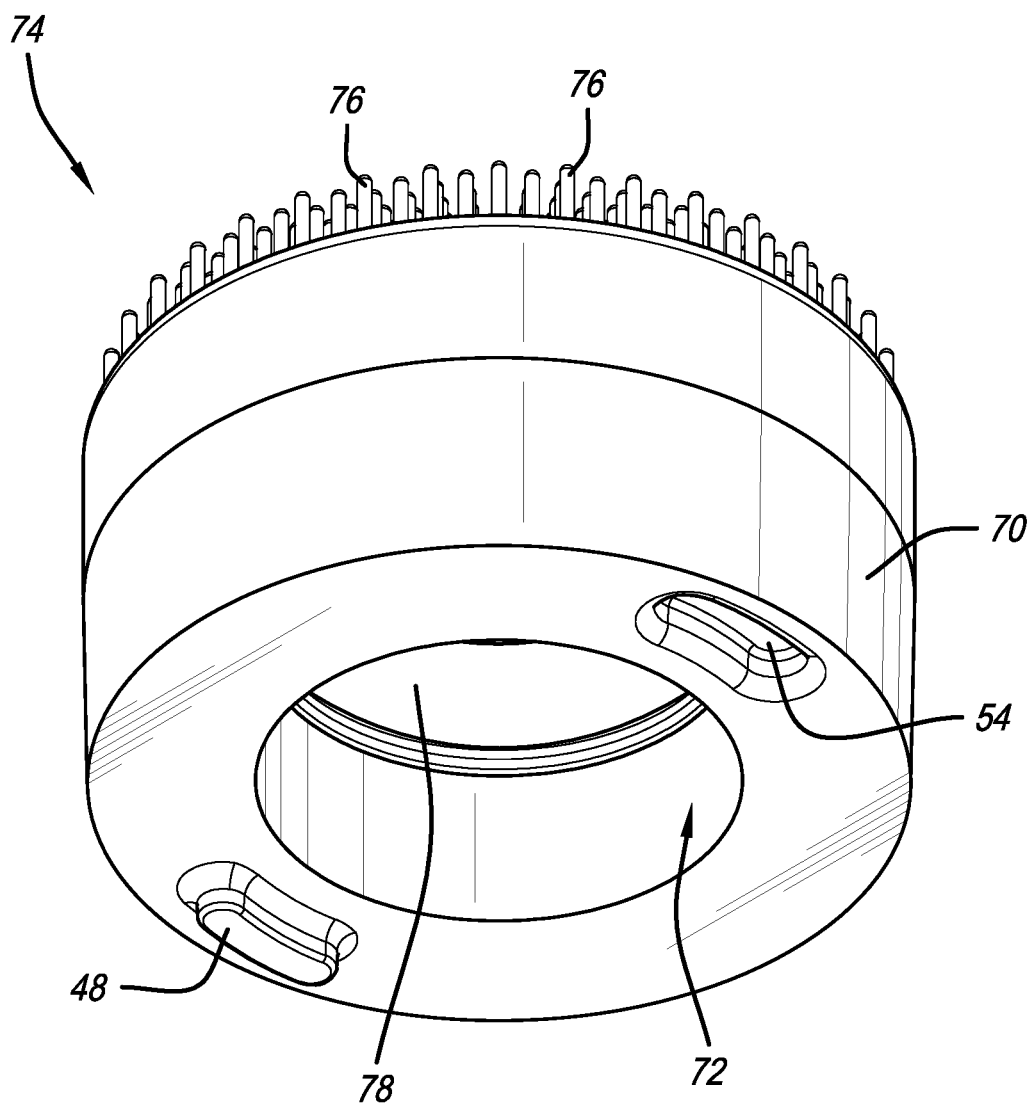
FIG. 21 is a bottom perspective view of the cleansing attachment.
Figure 22:
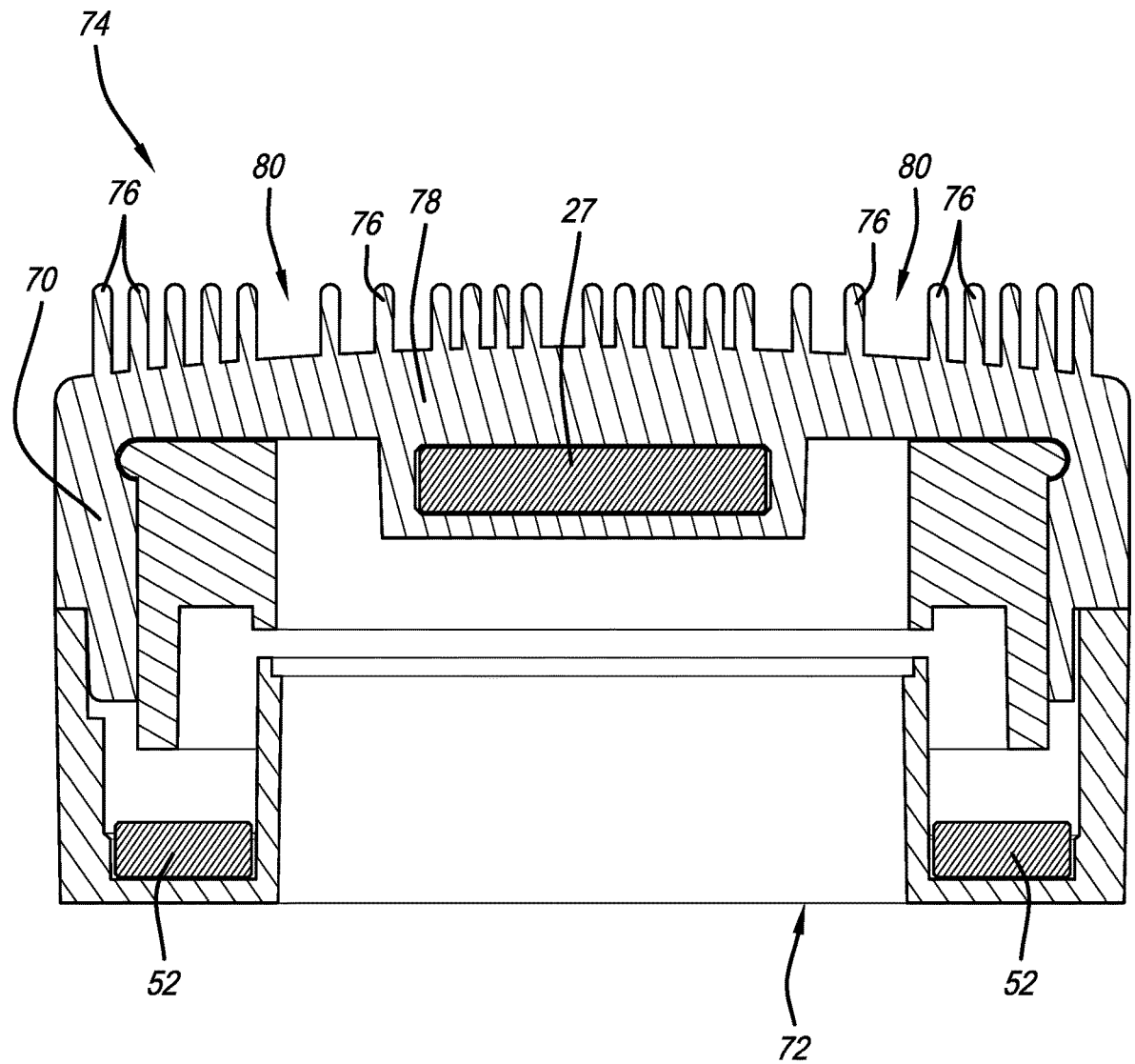
FIG. 22 is a cross-section of the cleansing attachment.

FIGS. 12, 21 and 22 shows another type of cap module referred to herein as a cleansing cap module or cleansing attachment 74 that includes a plurality of bristles 76 thereon. The cleansing attachment 74 includes a main body portion 70 and recess that receives the attachment member 26 when the cleansing attachment 74 is fitted on the module seat 50. The cleansing attachment 74 may also include (but preferably does not include) an electrical connection just like the ring module 18 described above. The cleansing attachment 74 preferably also includes a magnet 27 therein that is magnetically attracted to and connects to the magnet 27 in the attachment member 26. In a preferred embodiment, the main body portion 70 preferably includes the complementary securement protrusion 48 and recess 54, like the other therapy modules 11, that mate with the securement protrusion 48 and recess 54 on the module seat 50. Therefore, the cleansing cap module is configured to be removably secured to both the attachment member 26 (e.g., via magnets) and to the module seat 50 (e.g., via the complementary securement protrusions and recesses and set of magnets 52).

In a preferred embodiment, the cleansing attachment 74 includes a central section 76 that is flexible (for example, it may be made of silicone, rubber or other flexible material). Therefore, during use, when the attachment member 26 reciprocates, the central section 78 flexes. In other words, because the magnets 52 are holding the base of the main body portion 70 on and against the module seat 50, the central section 78 flexes and moves with each stroke of the attachment member 26. Therefore, the base of the main body portion 70 remains magnetically secured to the module seat 50 while the attachment member 26 reciprocates against the central section 78, therefore moving or percussing the central section 78 and the bristles 76 thereof against the user's skin. Essentially, the central section 78 is a flexible membrane that moves with the reciprocating attachment member 26. As shown in FIG. 22, the cleansing attachment 74 includes a groove 80 between the inner bristles 76 associated with the central section 78 and the outer bristles 76 that are located radially outwardly from the central section 78. The inner bristles move with the central section 146 and the outer generally bristles remain stationary during reciprocation. A cleansing formulation can be placed on the bristles 76 during use.

In another embodiment, the magnets 52 around the base can be omitted and the entire cleansing attachment 74 can reciprocate. The complementary securement protrusions and recesses can also be omitted since connection is made between the central magnet 27 and the magnet in the attachment member 26.

FIGS. 13-16 show a preferred embodiment system for attaching a component with microfiber material thereon (referred to herein as a skin treatment member 88) to the reciprocating attachment 19. In a preferred embodiment, the skin treatment member 88 includes lotion or some type of skin treatment ointment or fluid thereon and, therefore, is packaged in a pod member 90 that includes a container portion 92 and a lid 94. In a preferred embodiment, the skin treatment member 88 includes a generally ring shaped main body portion 96 and a delivery portion 98 that is preferably made of microfiber and includes the lotion thereon.

In a preferred embodiment, the skin treatment member 88 is attachable or securable to the reciprocating attachment 19. Preferably, the main body portion 96 includes one or more ridge members 100 on the inside surface thereof and extending inwardly that are received in one or more grooves 102 defined in the outer surface of the reciprocating attachment 19. The skin treatment member 88 preferably also includes a handle or tab 106 extending from the main body portion 96 that aids with attachment and removal of the skin treatment member 88 from the reciprocating attachment 19. In use, the skin treatment member 88 is removed from the pod member 90 (by peeling back the lid 94) and the treatment member is placed or seated on the reciprocating attachment 19. It will be appreciated that the main body portion 96 is made of a flexible material (such as plastic) so the ridge members 100 flex over the reciprocating attachment 19 and snap into the groove 102 on the outer surface of the reciprocating attachment. The delivery portion stretches across or spans the top or outer contact surface of the reciprocating attachment 19. The delivery portion 98 is then placed against the user's face and the device is activated such that the reciprocating attachment 19 (also referred to herein as a mallet) with the treatment member 88 thereon vibrates or percusses against the user's skin. After user, the use can pull on the tab 106 to separate the treatment member 88 from the mallet 19. As shown in FIG. 11, the skin treatment member 88 can be placed on the mallet 19 when the ring module 18 is on the device. Therefore, the LED light therapy can be used simultaneously with the vibration therapy and the treatment member therapy. The groove 102 is preferably located further from the module seat 50 than the outer surface 41a or outside of the ring module so that the skin treatment member 88 secured in the groove can reciprocate outside of the ring module.

Figure 17C:
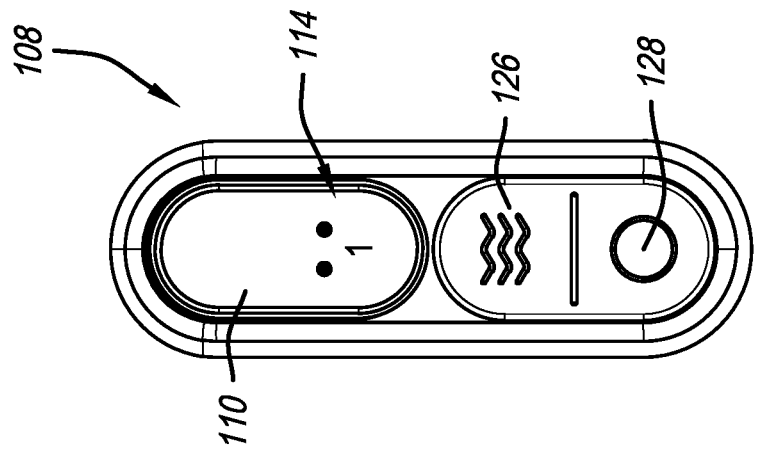
FIG. 17C is a view showing the user interface and display with the micro-current cap module symbol illuminated.
Figure 17B:
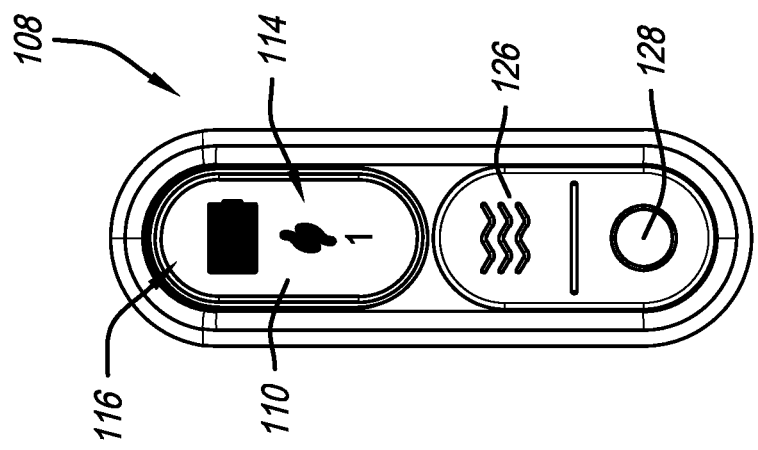
FIG. 17B is a view showing the user interface and display with the heat ring module symbol and battery symbol illuminated.
Figure 17A:
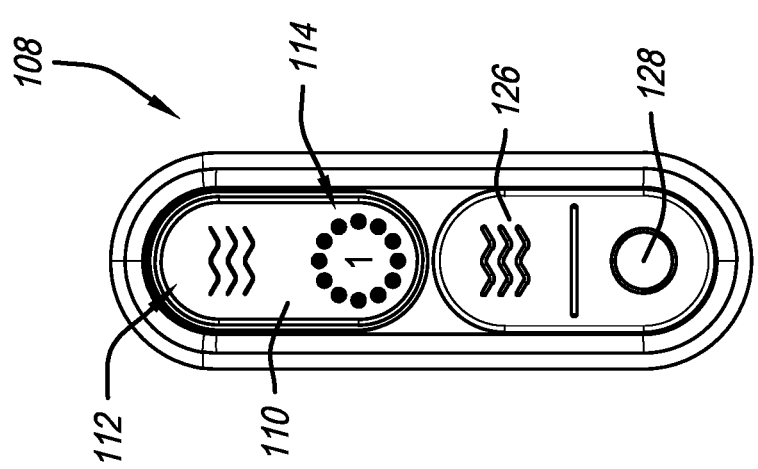
FIG. 17A is a view showing the user interface and display with the light ring module symbol and vibration symbol illuminated.

FIGS. 17A-17C show a control center 108 (or user interface—UI) that includes a display screen 110 and one or more buttons and/or switches that can be used for controlling the device 12 and the various therapy modules 11. The buttons can control different modes, different intensities, etc. In a preferred embodiment, the control center includes display screen 110, motor toggle button 126 (for toggling through different frequencies or speeds for the attachment member 26 and any reciprocating attachment thereon), module toggle button 128 (for toggling through different intensities or options for the therapy modules electrically connected to the device) and a power switch 16. FIG. 17A shows the display screen 110 with the motor speed level 112 at the top and the therapy module level 114 (with the light ring module symbol thereon) at the bottom. FIG. 17B shows the display screen 110 with the battery level 116 at the top and the therapy module level 114 (with the heat ring module symbol thereon) at the bottom. FIG. 17C shows the display screen 110 with nothing on the top and the therapy module level 114 (with the micro-current symbol thereon) at the bottom. Other symbols and the like that can be shown in the display screen include Bluetooth. It will be appreciated that the control center 108 is in data communication with the controller and associated components for controlling the device 12. Preferably, the device can recognize, sense or determine what type of therapy module has been seated on and electrically connected to the device. The information or data regarding the type of module is preferably communicated through the two prongs allocated for data communication. This allows the module toggle button 128 to toggle through the modes of the proper module and for the proper therapy module level to be displayed on display 110. Furthermore, in use, when a cap module (e.g., micro-current module 118) is seated on the module seat and electrically connected to the device, the motor is not activated (to reciprocate the attachment member) because the attachment member and magnet seat is located inside the cap module. This prevents the attachment member 26 from reciprocating within the cap module. When a ring module is seated on the device, the motor can be activated so that the reciprocating attachment can reciprocate within the central opening of the ring module.

It will be appreciated that all or some of the components discussed herein can be contained, sold or distributed in a kit. In other words, the vibration therapy system can be provided to users as a kit (e.g., within a case, box, bag or the like). The kit can include the vibration therapy device, one or more reciprocating attachments and one or more therapy modules. For example, an exemplary kit includes the device, the light ring module, the micro-current cap module, the reciprocating attachment with the groove therearound and charger all within a case or container.

Figure 18:
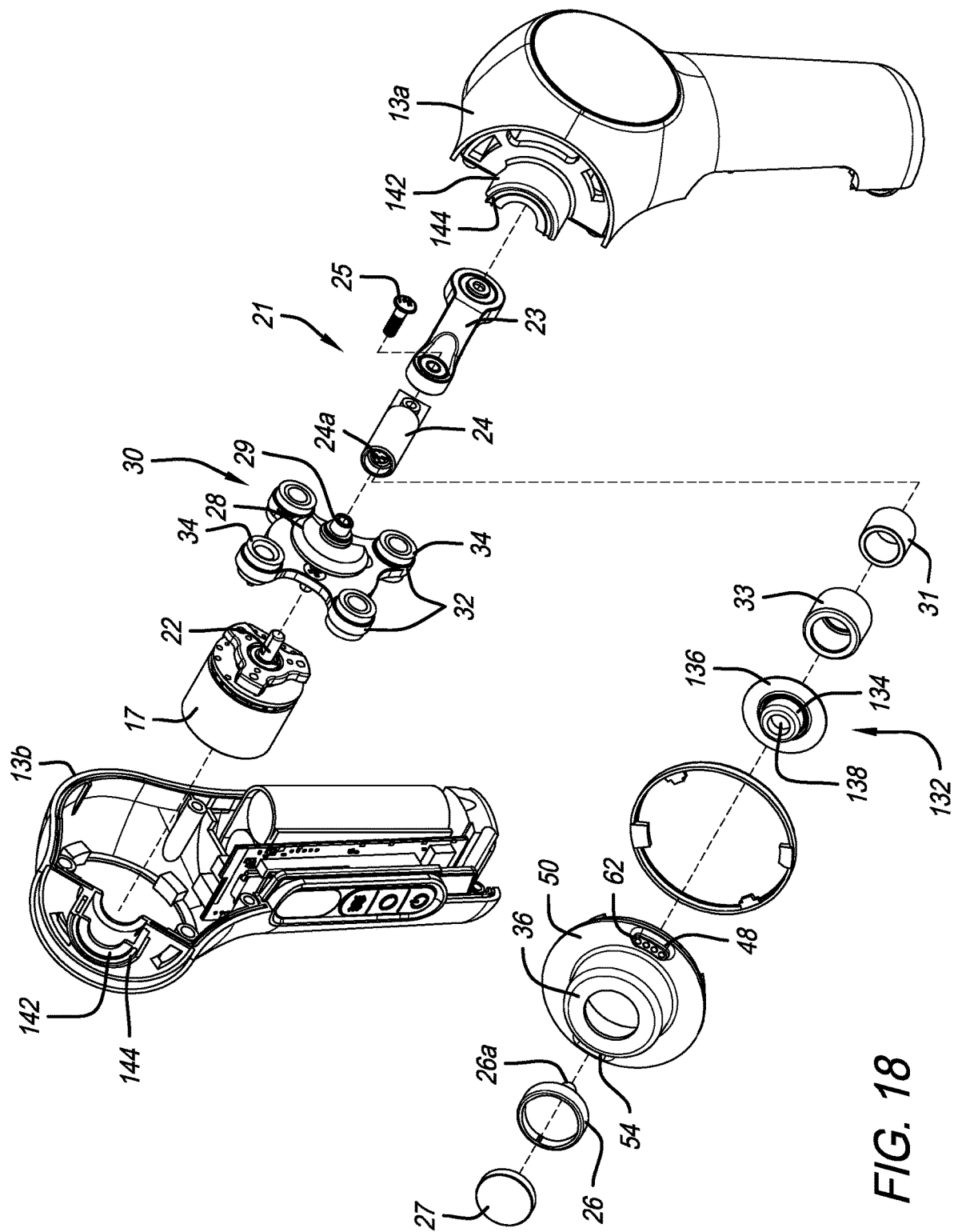
FIG. 18 is an exploded view of a vibration therapy device in accordance with a preferred embodiment of the present invention.
Figure 19:
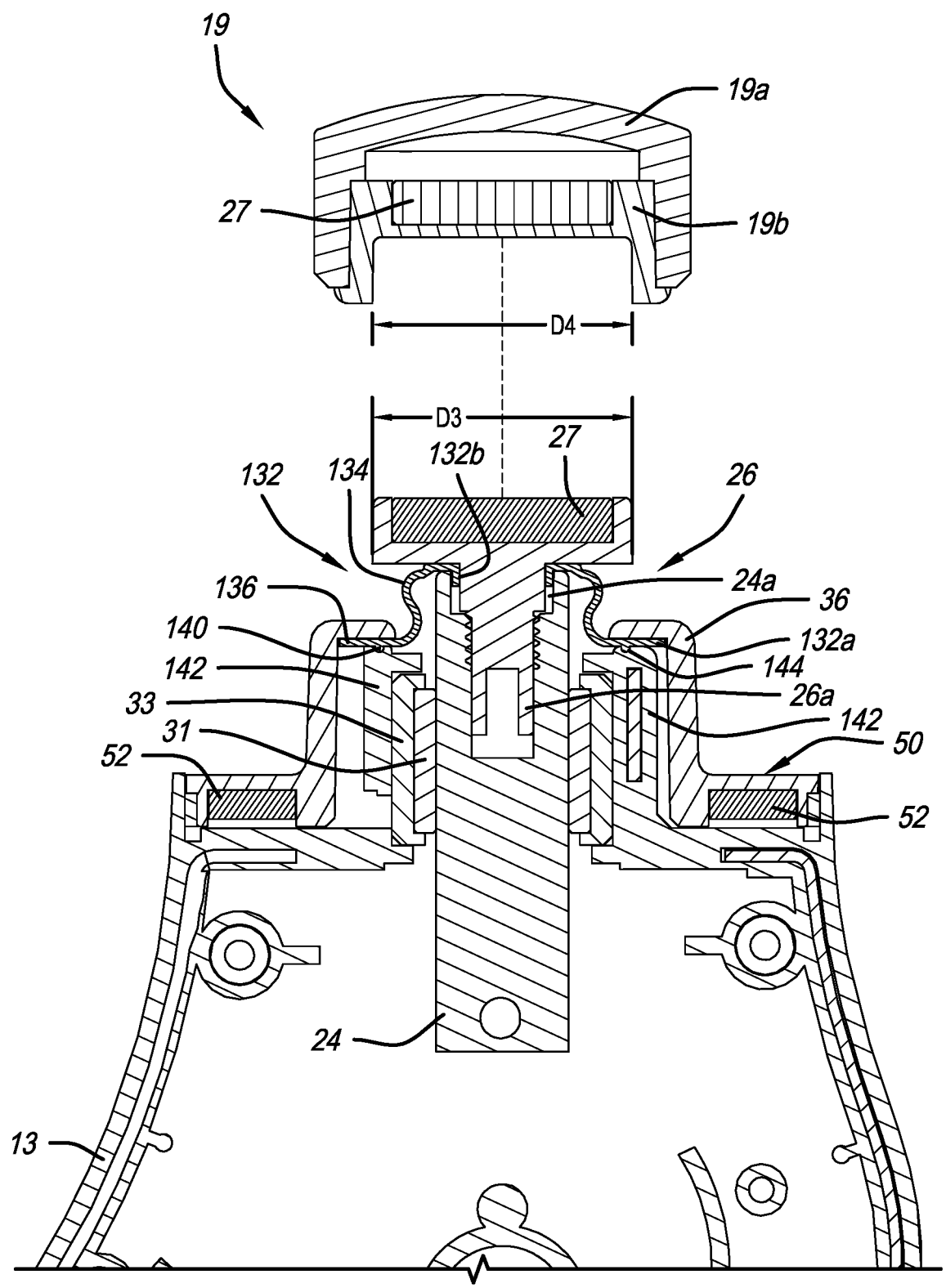
FIG. 19 is a cross-section of a portion of the vibration therapy device of FIG. 18 with a reciprocating attachment exploded therefrom.
Figure 20:
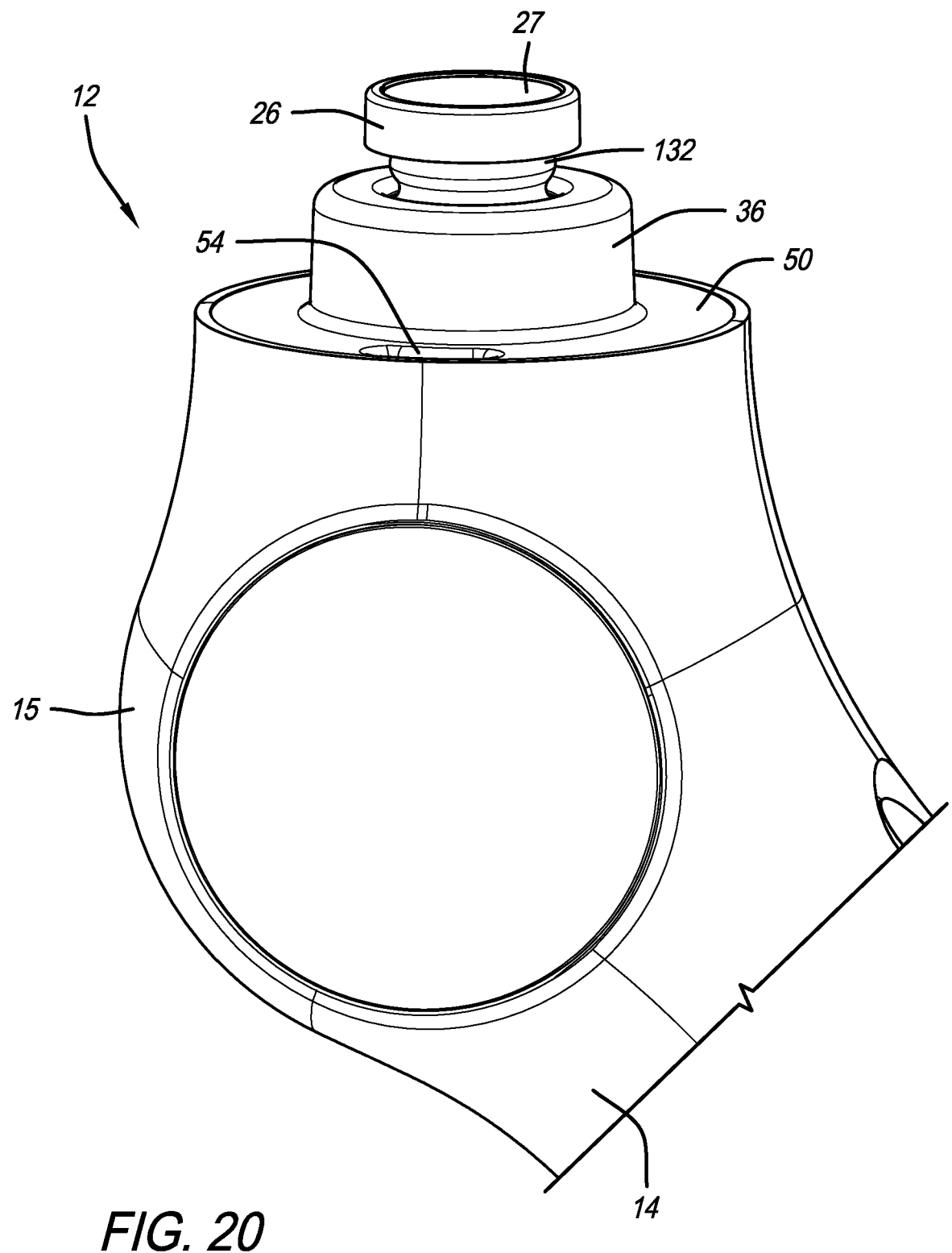
FIG. 20 is perspective view of a portion of the vibration therapy device showing the flexible sleeve that provides water resistance.

FIGS. 18-20 show another preferred embodiment of the vibration therapy device 12. All disclosure related to other embodiments herein is also relevant to the embodiment shown in FIGS. 18-20. As shown in FIG. 19, in a preferred embodiment, the reciprocating attachment 19 includes an attachment member recess 130 defined therein. The attachment member 26 is received in the attachment member recess 130. The attachment member 26 defines an attachment member diameter D3 and the attachment member recess 130 defines an attachment member recess diameter D4. The attachment member diameter D3 is smaller than the attachment member recess diameter D4, which allows the reciprocating attachment 19 to be received on the attachment member 26. Also, the first and second magnets 27 in the attachment member and the reciprocating attachment 19 secure the reciprocating attachment 19 on the attachment member 26. The first and second magnets 27 are strong enough to hold the reciprocating attachment 19 on the attachment member 26 during reciprocation, and, in particular, with the reciprocation occurring in the any of the frequency and amplitude ranges discussed herein. In particular, the magnets prevent the reciprocating attachment 19 from disconnecting from the attachment member 26 during reciprocation. In a preferred embodiment, the amplitude range is between 1.0 mm and 5.0 mm and in a more preferred embodiment, the amplitude range is between 2 mm and 4 mm. In a most preferred embodiment, the amplitude range is between 2.9 mm and 3.1 mm. Preferably, the frequency is between 25 Hz and 45 Hz when operating at any of the amplitudes (or strokes) discussed herein. These figures can also be framed in terms of linear velocity, which depends on the distance traveled by an object with respect to time taken. The linear equation or the linear velocity formula is given by v=x/t, where, v=linear velocity, x=distance covered and t=time taken to cover the distance(x). Linear velocity is often measured using SI unit meter per second or m/s. It will be appreciated that, in a preferred embodiment, at speeds or frequencies between 1700 rpm/28.3 Hz, 1750 rpm/29.2 Hz, 2100 rpm/35 Hz, 2400 rpm/40 Hz and 3000 rpm/50 Hz and an amplitude of between 1.0 mm and 5.0 mm, the linear velocity is between 0.06 m/s and 0.5 m/s. In a more preferred embodiment, the linear velocity is between 0.11 m/s and 0.4 m/s.

In a preferred embodiment, the vibration therapy device 12 includes a flexible sleeve 132 that includes a sleeve portion 134, an annular flange 136, a central opening 138, an annular ridge 140 and proximal and distal ends 132a and 132b respectively. As shown in FIG. 19, the flexible sleeve 132 surrounds the distal end of the reciprocating shaft 24. In a preferred embodiment, the distal end of the flexible sleeve 132b is secured to the attachment member 26 and the proximal end of the flexible sleeve 132a is secured to and/or within the housing 13 or a component thereof. The flexible sleeve 132 provides water resistance and helps prevent moisture from getting into the housing interior.

As discussed above, the reciprocating shaft 24 includes an opening 24a that receives the shaft 26a of the attachment member 26. In the embodiment shown in FIG. 19, the interior of opening 24a and the exterior of shaft 26a include complementary threading to secure the shaft 26a within the opening 24a. In a preferred embodiment, the distal end of the flexible sleeve 132b is secured between the distal end of the reciprocating shaft and the attachment member 26, and, more particularly, the distal end of the flexible sleeve 132b extends into opening 24a and is secured between the inner surface of the opening 24a and the outer surface of shaft 26a. As discussed above, the housing includes a protrusive portion 36 that is part of cap 35. Each of the housing halves 13a and 13b include part of a nose portion 142 that includes an annular groove 144 defined therein. The annular groove 144 receives the annular ridge 140 that extends downwardly from the annular flange 136 of the flexible sleeve 132, as is best shown in FIG. 19. the housing includes a protrusive portion, wherein the proximal end of the flexible sleeve is secured by the protrusive portion. As shown in FIG. 19, the proximal end of the flexible sleeve 132a (which is part of the annular flange 136) is sandwiched between the protrusive portion 36 and the nose portion 142.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

The teachings of the disclosure provided herein can be applied to other systems, not necessarily the system described above. The elements and acts of the various embodiments described above can be combined to provide further embodiments. Any measurements or dimensions described or used herein are merely exemplary and not a limitation on the present invention. Other measurements or dimensions are within the scope of the invention.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A vibration therapy device, comprising:
   a housing that includes a handle portion and a head portion;
   an electrical source;
   a motor positioned in the housing;
   a switch for activating the motor;
   a push rod assembly operatively connected to the motor, wherein the push rod assembly comprises:
      a reciprocating shaft having a distal most end and an opening defined at the distal most end; and
      an attachment member coupled to the distal most end of the reciprocating shaft, the attachment member comprising a shaft extending into the opening of the reciprocating shaft and a magnet seat having a first magnet received therein,
      wherein the reciprocating shaft is configured to reciprocate in response to activation of the motor, such that the attachment member has a linear velocity between 0.06 m/s and 0.5 m/s; and
   a reciprocating attachment removably received on the attachment member, wherein the reciprocating attachment includes a second magnet that is magnetically attracted to the first magnet to secure the reciprocating attachment on the attachment member; and
   a flexible sleeve that includes a proximal end and a distal most end,
      wherein the flexible sleeve at least partially surrounds the reciprocating shaft, and
      wherein the distal most end of the flexible sleeve is secured to the attachment member and the proximal end of the flexible sleeve is secured to the housing.

2. The vibration therapy device of claim 1, wherein the reciprocating attachment includes an attachment member recess defined therein,
   wherein the attachment member is received in the attachment member recess,
   wherein the attachment member defines an attachment member diameter and the attachment member recess defines an attachment member recess diameter,
   wherein the attachment member diameter is smaller than the attachment member recess diameter, and
   wherein the first and second magnets secure the reciprocating attachment on the attachment member during reciprocation.

3. The vibration therapy device of claim 2, wherein the head portion comprises a module seat,
   wherein the vibration therapy device further comprises a ring module removably secured to the module seat,
   wherein the ring module includes a central opening that defines a central opening diameter,
   wherein the reciprocating attachment defines a reciprocating attachment diameter, and
   wherein the central opening diameter is larger than the reciprocating attachment diameter, such that the reciprocating attachment is configured to reciprocate within and relative to the ring module.

4. The vibration therapy device of claim 3, wherein the ring module is in electrical communication with the electrical source,
   wherein the module seat includes a first electrical connector, and
   wherein the ring module includes a second electrical connector in electrical communication with the first electrical connector.

5. The vibration therapy device of claim 1, wherein the reciprocating shaft includes an opening in the distal most end thereof,
   wherein the attachment member includes a shaft that is received in the opening in the reciprocating shaft, and
   wherein the distal most end of the flexible sleeve is secured between the distal most end of the reciprocating shaft and the attachment member.

6. The vibration therapy device of claim 1, wherein the reciprocating shaft is configured to reciprocate in response to activation of the motor such that the attachment member has a linear velocity between 0.11 m/s and 0.4 m/s.

7. The vibration therapy device of claim 1, wherein the head portion comprises a module seat configured to removably receive a therapy module, wherein the module seat surrounds the attachment member, and
wherein the module seat includes a set of magnets configured to removably secure the therapy module.

8. A therapy device, comprising:
a housing that includes a handle portion, a head portion, and a module seat defined on the head portion, wherein the module seat includes a first set of magnets, and wherein the module seat includes a first securement protrusion extending therefrom and includes a first securement recess defined therein;
an electrical source;
a therapy module removably secured to the module seat, wherein the therapy module includes a second set of magnets that are magnetically attracted to the first set of magnets,
wherein the therapy module includes a second securement protrusion extending therefrom and includes a second securement recess defined therein,
wherein the first securement protrusion is received in the second securement recess, and
wherein the second securement protrusion is received in the first securement recess;
a motor positioned in the housing;
a switch for activating the motor; and
a push rod assembly operatively connected to the motor, wherein the push rod assembly comprises:
a reciprocating shaft having a distal most end and an opening defined at the distal most end; and
an attachment member coupled to the distal most end of the reciprocating shaft, the attachment member comprising a shaft extending into the opening of the reciprocating shaft and a magnet seat having a magnet received therein,
wherein the therapy module includes a central opening defined therein, and wherein the attachment member extends into the central opening; and
a flexible sleeve that includes a proximal end and a distal most end,
wherein the flexible sleeve at least partially surrounds the reciprocating shaft, and
wherein the distal most end of the flexible sleeve is secured to the attachment member and the proximal end of the flexible sleeve is secured to the housing.

9. The therapy device of claim 8, wherein one of the first securement protrusion and the second securement recess includes female electrical contacts and the other of the first securement protrusion and second securement recess includes male electrical contacts, and wherein connection of the male electrical contacts and female electrical contacts provides electrical communication between the electrical source and the therapy module.

10. The therapy device of claim 9, wherein the therapy module provides at least one of cold therapy, heat therapy, LED light therapy, microcurrent therapy, photobiomodulation therapy, radio frequency therapy, cleansing therapy, or ultrasound therapy.

11. The therapy device of claim 10, wherein the therapy module is configured to provide the cold therapy at a temperature range between about 65 degrees Fahrenheit to about 78 degrees Fahrenheit.

12. The therapy device of claim 10, wherein the therapy module is configured to provide the heat therapy at a temperature range between about 95 degrees Fahrenheit to about 109 degrees Fahrenheit.

13. The therapy device of claim 9, wherein the male electrical contacts include four prongs, and wherein two of the prongs provide electrical communication and two of the prongs provide data communication.

14. A vibration therapy device, comprising:
a housing that includes a handle portion and a head portion;
an electrical source;
a motor positioned in the housing;
a switch for activating the motor;
a push rod assembly operatively connected to the motor, wherein the push rod assembly comprises:
a reciprocating shaft having a distal most end and an opening defined at the distal most end; and
an attachment member coupled to the distal most end of the reciprocating shaft, the attachment member comprising a shaft extending into the opening of the reciprocating shaft and a magnet seat having a magnet received therein; and
a flexible sleeve that includes a proximal end and a distal most end, wherein the flexible sleeve at least partially surrounds the reciprocating shaft, wherein the distal most end of the flexible sleeve is secured to the attachment member and the proximal end of the flexible sleeve is secured to the housing.

15. The vibration therapy device of claim 14, wherein the reciprocating shaft includes an opening in the distal most end thereof,
wherein the attachment member includes a shaft that is received in the opening in the reciprocating shaft, and
wherein the distal most end of the flexible sleeve is secured between the distal most end of the reciprocating shaft and the attachment member.

16. The vibration therapy device of claim 15, wherein the housing includes a protrusive portion, and wherein the proximal end of the flexible sleeve is secured by the protrusive portion.

17. The vibration therapy device of claim 16, wherein the flexible sleeve includes an annular ridge extending therefrom that is received in a groove in the housing.

18. A vibration therapy device, comprising:
a housing that includes a handle portion, a head portion and a module seat defined on the head portion, wherein the module seat includes a first set of magnets;
an electrical source;
motor positioned in the housing;
a switch for activating the motor;
a push rod assembly operatively connected to the motor, wherein the module seat surrounds the push rod assembly, and wherein the push rod assembly comprises:
a reciprocating shaft having a distal most end and an opening defined at the distal most end; and
an attachment member coupled to the distal most end of the reciprocating shaft, the attachment member comprising a shaft extending into the opening of the reciprocating shaft and a magnet seat having a first magnet received therein; and
a cleansing attachment removably received on the attachment member,
wherein the cleansing attachment includes a second magnet that is magnetically attracted to the first magnet to secure the cleansing attachment on the attachment member,
wherein the cleansing attachment includes a second set of magnets that are magnetically attracted to the first set of magnets to removably secure the cleansing attachment to the module seat,
wherein the cleansing attachment includes a central section, and wherein when the attachment member reciprocates, the central section flexes.

19. The vibration therapy device of claim 18, wherein the module seat includes a first securement protrusion extending therefrom and includes a first securement recess defined therein,
- wherein the cleansing attachment includes a second securement protrusion extending therefrom and includes a second securement recess defined therein,
- wherein the first securement protrusion is received in the second securement recess, and
- wherein the second securement protrusion is received in the first securement recess.

\* \* \* \* \*